United States Patent [19]
Nicolas et al.

[11] Patent Number: 5,830,722
[45] Date of Patent: Nov. 3, 1998

[54] CLOSTRIDIUM BIFERMENTANS DNA FRAGMENT BEARING GENES CODING FOR PROTEINS LINKED TO AN INSECTICIDAL ACTIVITY

[75] Inventors: Luc Nicolas, Polynesie; Jean-Francois Charles, Saint-Mandé; Armelle Delecluse, Thiers-sur-Theve; Frederique Barloy, Paris, all of France

[73] Assignee: Institut Pasteur, Paris Cedex, France

[21] Appl. No.: 569,166

[22] PCT Filed: Jun. 24, 1994

[86] PCT No.: PCT/FR94/00768

§ 371 Date: Jul. 5, 1996

§ 102(e) Date: Jul. 5, 1996

[87] PCT Pub. No.: WO95/00639

PCT Pub. Date: Jan. 5, 1995

[30] Foreign Application Priority Data

Jun. 25, 1993 [FR] France .................................... 93 07795

[51] Int. Cl.[6] .............................. C12N 15/31; C12N 1/21; C07K 14/33; C07H 21/04
[52] U.S. Cl. ..................................... 435/172.1; 435/252.3; 435/320.1; 435/419; 514/2; 530/300; 536/23.7
[58] Field of Search ........................... 424/832; 435/69.1, 435/91.4, 240.2, 252.3, 320.1, 172.1, 419; 514/2; 530/300, 350, 825; 536/23.1, 23.71, 23.7

[56] References Cited

PUBLICATIONS

Porter, Mosquitocidal toxins, genes and bacteria: the hit squad. Parasitology Today. vol. 12(5):175–179, Apr. 25, 1996.

*Primary Examiner*—Nancy Degen
*Assistant Examiner*—William Sandals
*Attorney, Agent, or Firm*—Oblon, Spivak, McClelland, Maier & Neustadt, P.C.

[57] ABSTRACT

A nucleotide sequence having the following properties: it includes all or part of DNA fragment XbaI of 7 kb shown in FIG. 4A, as obtained from plasmid pCBM1 filed with the CNCM on Jun. 15, 1993 under no. I-1317; it hybridises with oligonucleotide probe 18A (TGT GAA GTI AAT TGT GA) SEQ ID NO:1 and/or oligonucleotide probe 16A (TTT CAT ATI GAA GCI GTI AAT GAA GG) SEQ ID NO:2 and/or at least one of probes 66A (ATG AAT ACI AAT ATI TTT TCI ACI AA) SEQ ID NO:3 or 66B (TC IGG TTC ICC ATA IAT CCA TTC ATC) SEQ ID NO:4 under stringent conditions; and it codes for a protein, polypeptide or peptide capable of participating in the toxic activity of the expression products of fragment XbaI of 7 kb against Diptera larvae and mosquito or sandfly larvae in particular. The polypeptides encoded by said sequence and their use in larvicidal compositions are also disclosed.

49 Claims, 24 Drawing Sheets

ITALIC: SITE FOR THE pUC19 POLYLINKER

```
                                                              Sau3A I
                                                              Mbo I
                                                              Dpn I
                                                              BstY I
                                                              AlwN I
         Gsu I  Ssp I                                         Alw I
AAGTTCTGGAGAAATATTATACATTTCTCATATCACTAATTGGTATATCTCATCTATAAATTTACAGGATCTGAATAAA        320
TTCAAGACCTCTTTATAATATGTAAAAGAGTAGTGATTAACCATATAGAGTAGATATTTAAATGTCCTAGACTTATTT
       |        |                                                         |||
       246      253                                                       306
                                                                        308
                                                                        308
                                                                        309
                                                                        309
                                                                        309

Mae I
                                                              Nla III
CTTTTCTTGTGAGAGTTTGCATATTTATAGGTTTATCATATCTTTGTATCATATATTGGGAAAATAGAAATCATGTCTA        400
GAAAAGAACACTCTCAAACGTATAAATATCCAAATAGTATAGAAACATAGTATATAACCCTTTTATCTTTAGTACAGAT
                                                                          |   |
                                                                          393 398

Fok I
|
GGATGTAAAAAGTCATAAATCTACAATATCTG    432
CCTACATTTTTCAGTATTTAGATGTTATAGAC
|
401
```

FIG. 6D

```
                        Sau3A I
                        Mbo I
                        Dpn I
                     Sec I
                     Scrf I
                     Nci I
                     Msp I
                     Hpa II
                    Xma I
                    Sma I
                    Sec I
                    Scrf I
              Nla IV    Alw I
              Kpn I    Nla IV
        Alu I    Nci I
        Sac I  Rsa I   BstY I
        HgiA I    Bcn I
        Bsp1286 I  Bcn I    Xba I
        Bap II   Ava I   Mn l I                         SfaN I
        Taq I   Ban I   BamH I                          Fok I
       EcoR I   Asp718  Alw I  Mae I             Mbo II
        I   I  II   II  II   II  I  II                   I    II
GGTTAGTGAATTCGAGCTCGGTACCCGGGGATCCTCTAGAAATTTATTATTTTATGGTATTGAAGATGGATGCTCTGATA  80
CCAATCACTTAAGCTCGAGCCATGGGCCCCTAGGAGATCTTTAAATAATAAAATACCATAACTTCTACCTACGAGACTAT
        I · I  II    II  II    II  I  II  ·       ·        · I     II·      ·
        8      20     29   36                           62
        12     20     29                                      68
        14      24    33                                      69
        14       25    35
        14      24
        14    21    29
        15     24
        20     29
        20     30
        24
        24
        24
        24
         25
         25
         25
         25
         25
          30
          30
          30
```

FIG. 6H

```
            Mse I                                                                   Tth111 II
         Dra I
     Mae III                                                                           |
       | ||                                                                             |
CAACAAGGGTCACTTTAAAAATAGATACATAGATACTGAAATTGAAAAAGAAATAATCAAACATCTATTGAATACAGGAA   400
GTTGTTCCCAGTGAAATTTTATCTATGTATCTATGACTTTAACTTTTTCTTTATTAGTTGTAGATAACTTATGTCCTT
     |   | |                                                                  |
    329 334                                                                  378
        335

ACC  403
TGG
```

FIG. 6J

NH-2 TERMINAL SEQUENCE P 18

Met asn asn cys glu val asn cys glu asn thr glu glu asn lys tyr arg ala tyr

NH-2 TERMINAL SEQUENCE P 16 arg gln trp val lys phe his ile glu ala val asn glu gly leu lys ile arg asn ala ser

INTERNAL SEQUENCE P 16 leu lys trp gly lys phe his asp pro asn asn lys asp ile pro ile ser pro glu asp ile ser lys ile asn ile glu lys his asp thr ala ile ile ala ser ser gly lys glu asn thr ala

INTERNAL SEQUENCE P 18 ser gly thr glu gly val phe tyr ile cys asp glu thr STOP

FIG.7

```
CBMAA.dat              check: 5932    from: 1      to:  100
SW:C03_NAJNA           check: 3526    from:1545    to: 1651
Q01833 naja naja (indian cobra). complement c3 precursor.  10/93
Gaps: 5  Quality: 37.5  Ratio: 0.375  Score: 20  Width: 5

1 ZADINMNNNCEVNCENTEENKYRAYRQWV...KFHIEAVNEGLKIRNASL   47
     ::|| :: ||  :  ::|: :|||  ::|   |||| ||: | :|: |:|
1545 GNDIYFMDVLEVIKGGTDRNAQAKARQYVSQRKCQ.EALN..LKLDNDYL 1591

48 KWGKFHD..PNNKDIPISPEDISKI....NIEKHDTAIIASSGKENTASG   91
     |  ||| |  |    |   | ::|       |:|: :  : ::||| :::
1592 IWGLSSDLWPMKDDISYLITKNTWIERWPNEDECQDEEFQNLCDDFAQLS 1641

92 TEGVFYICD  100
     ::|: :||
1642 NTLTIFGCP 1650
```

FIG.11A

```
CBMAA.dat              check: 5932   from: 1     to: 100
SW.AAC2_DICDI          check: 4701   from: 297   to: 448
P14196 dictyostelium discoideum (slime mold) Gaps: 1
Quality: 41.3  Ratio: 0.413  Score: 19  Width: 36

1 ZADINMNNNCEVNCENTEENKYRAYRQWVKFHIEAVNEGLKIRNASLKWG   50
       ..  ||| .: |.|.:|          .| :|. :|. . ||
312 NNTNNNNNNNTNNNNNINNNNNNNNTNNNNNANNQNTNNNNMGNNSN.   361

51 KFHDPNNKDIPISPEDISKINIEKHDTAIIASSGKENTAS..........  90
     |||: .::       |   :..  : : .|:.| |.|
362 NNNNPNNNNHQNNNNNNTSNNSNTTTATTTAPGGNNLTNSLNNAGNLGNL  411

91 GTEGVFYICD 100
    | ..::  |
412 GRVSGLHSSD 421
```

FIG.11B

```
CBMAA.dat                  check: 5932   from: 1     to: 100
SW:AMY_CLOAB               check: 275    from: 354   to: 469
P23671 clostridium acetobutylicum. putative alpha-amylase
Gaps: 6  Quality: 33.6  Ratio: 0.357  Score: 18  Width: 14

7 NNNCEVNCENTEENKYRAYRQWVKFHIEAVNEGLKIRNASLKWGKFHDPN  56
    .  . :  . : : . :  .  :  : .: .  : . .  ::
354 TNGSSWDNNNNNNWTLNTWSSVPKVQVTPAPEA..CKQISVYYNGSLASS 401

57 NKDIPI.........SPEDISKIN..IEKHDTAIIASSG..KENTA....S  90
    : :.:           :  :.::    .  ::. : : ::        :
402 ASNITLHWGCNGFTSPQDINMVKQADGRWLANITLPSGCYNVNMAFKDQS 451

91 GT......EGVFYICD 100
    ::      :
452 GTWDNNNSNNYNFSS  466
```

FIG.11C

CLOSTRIDIUM BIFERMENTANS DNA FRAGMENT BEARING GENES CODING FOR PROTEINS LINKED TO AN INSECTICIDAL ACTIVITY

The invention relates to new toxins isolated from a strain of anaerobic bacterium of the species *Clostridium bifermentans*. The strain CH18 of *Clostridium bifermentans* serovar *malaysia* (*Cbm*) has been described by H. de Barjac and M. Sebald, in C.R. Acad. Sci. Paris, vol. 310, series III, p. 383–387, 1990.

It exhibits a toxic activity during the sporulation phase via toxins having a larvicidal power against the larvae of arthropods, in particular of insects and especially against the larvae of Diptera, for example the larvae of mosquitoes or of similis. These particular Diptera are vectors of diseases or cause harmful effects.

Until now, toxins specific to bacteria of the species *Bacillus thuringiensis* or of the species *Bacillus sphaericus* were known for their entomopathogenic activity and especially their toxic activity against mosquito larvae (Nicolas (1992). Pes. agropec. bras., Brasilia, abr. 1992, 27, 37–46). In spite of the obvious benefit of these Bacillus toxins for controlling insects and especially insect larvae, the search for new toxins active against certain insects proved to be important especially with the aim of offering means for controlling the risk of development of resistance against these products with larvicidal activity. In this context, the inventors have detected the existence of a larvicidal activity in the bacterium of the species *Clostridium bifermentans*. In this regard, the invention proposes, for the first time, toxins present in anaerobic bacteria, which are capable of having a toxic activity and in particular a larvicidal activity against arthropods, and in particular insects of the Diptera type. The strain of *Clostridium bifermentans* serovariety *malaysia* used is harmless against the mammals and fish tested as well as against all aquatic organisms outside the natural target for the larvicidal activity of *Cbm* (Thiery et al. (1992) J. econ. Entomol. 85(5), 1618–1623). The existence of the larvicidal activity of *Cbm* has already been observed and associated, in the prior art, with sporulating cells (Charles et al. (1990) Res. Microbiol. 141, 721d–733). It has also been noted that this activity decreases very substantially after cell lysis because of inactivation by cellular proteases (Nicolas et al (1990). Appl. Microbiol. Biotechnol. 34, 36–41).

The subject of the invention is therefore nucleotide sequences encoding polypeptides capable of taking part in the toxic activity against the larvae of arthropods and in particular of insects, especially of Diptera such as mosquitoes and simuliids.

The invention also relates to these polypeptides as well as recombinant cells containing the nucleotide sequences and the nucleotide fragments of the invention, under conditions allowing their expression.

Also entering into the framework of the present application are antibodies which recognize the polypeptides of the invention, as well as compositions with larvicidal activity.

A nucleotide sequence of the invention is characterized by the following properties:
it comprises all or part of the 7 kb XbaI DNA fragment represented in FIG. 4A, as obtained from the plasmid pCBM1 deposited at CNCM on 15 Jun. 1993 under the No. I-1317;
it hybridizes with the oligonucleotide probe 18A (SEQ ID NO:1) (TGT GAA GTI AAT TGT GA) and/or with the oligonucleotide probe 16A (SEQ ID NO:2) (TTT CAT ATI GAA GCI GTI AAT GAA GG) and/or with at least one of the probes 66A (SEQ ID NO:3) (ATG AAT ACI AAT ATI TTT TCI ACI AA) or 66B (SEQ ID NO:4) (TC IGG TTC ICC ATA IAT CCA TTC ATC) under stringent conditions described in the experimental part;
it encodes a protein, a polypeptide or a peptide having the capacity to take part in the toxic activity of the products of expression of the 7 kb XbaI fragment against the larvae of Diptera and in particular the larvae of mosquitoes or of simuliids.

The toxic activity is defined within the frame-work of the invention in relation to the "target" on which it is desired to obtain this activity. This "target" is generally an arthropod and more particularly an insect, especially of the Diptera family and for example, a mosquito or simuliid larva.

It will be considered within the framework of the invention that a nucleotide sequence encodes a protein or a polypeptide having the capacity to take part in the toxic activity of the products of expression of the 7 kb XbaI fragment contained in the plasmid pCBM1 deposited at CNCM under the No. I-1317, provided that the deletion or the alteration of this sequence within the said plasmid results in a decrease or suppression of the toxic activity against the larvae of Diptera and in particular the larvae of mosquitoes or of simuliids, which is observed when this plasmid is introduced into a recombinant cell which does not have a larvicidal activity naturally.

Other recombinant cells, such as those described by Delecluse A. et al (1988) Mol. Gen. Genet. 214:42–47), can also be used.

The statement relating to the toxic activity against Diptera larvae should in no way be considered to be restrictive as regards the activity spectrum, the means of the invention. It constitutes solely a reference for the evaluation of the activity of the products of the invention.

The toxic activity can be evaluated by measuring the $LC_{50}$ (lethal dose for 50% of the insects or more generally of the "target" on which it is desired to evaluate the toxic activity).

Various tests have already been proposed in the prior art for detecting the larvidical activity of strains of bacteria capable of producing toxins. In this regard, reference may be made to the publication by Thiery, I. et al. (1992) Journal of American Mosquito Control Association, vol. 8, No. 3, 272–276.

Within the framework of the definition given above, the nucleotide sequence according to the invention may encode a protein, a polypeptide or a peptide which is necessary for inducing the larvicidal activity and/or may encode a protein, a polypeptide or a peptide which influences the level of expression of the toxicity against a given target. As stated above, tests carried out with recombinant cells lacking larvicidal activity naturally, transformed by the plasmid pCBM1 under conditions allowing the expression of the genes contained in the inserted DNA fragment, can be used as a basis for comparison to test the larvicidal activity of proteins or parts of proteins expressed by a nucleotide sequence according to the invention.

The terms "protein", "polypeptide" and "peptide" designate within the framework of the application, any amino acid sequence, it being possible for this sequence, in addition, to be modified by groups which are of a nonprotein nature. To simplify the text, these proteins, polypeptides and peptides will be included in the expression "polypeptides".

According to an advantageous embodiment of the invention, a specific nucleotide sequence is characterized in that it hybridizes with the four probes 16A, 18A, 66A and 66B, under stringent conditions. The stringent conditions referred to here are described in detail in the experimental part of the present application.

According to another embodiment of the invention, a specific sequence is characterized in that it hybridizes with the four probes 16A, 18A, 66A and 66B, under nonstringent conditions (less stringent compared with the conditions given later as stringent conditions).

The invention relates in particular to the nucleotide sequence characterized in that it is the 7 kb XbaI fragment of the plasmid pCMB1 deposited at CNCM under the No. I-1317.

According to a specific embodiment, the subject of the invention is a nucleotide sequence chosen from the chains designated by the expressions Seq1, Seq2.1, Seq2.2 or Seq3, and which are represented in FIG. 6.

The invention also relates to a nucleotide sequence characterized in that it hybridizes with one of the sequences described above, in that it is present in the DNA of a bacterium of the species *Clostridium bifermentans*, and in that it encodes a protein, a polypeptide or a peptide having the capacity to take part in a toxic activity against the larvae of Diptera and in particular against the larvae of mosquitoes or of simuliids.

The nucleotide sequences of the invention can be isolated for example from anaerobic bacteria of the species *Clostridium bifermentans* and in particular from the strain *Clostridium bifermentans malaysia*. They can also be synthesized chemically according to conventional techniques.

Moreover, these nucleotide sequences may consist of single-stranded or double-stranded DNA, of cDNA or of RNA.

The subject of the invention, according to a specific embodiment, is a nucleotide sequence characterized in that it contains fragments encoding the following amino acid sequences:
M N T N I F S T N L (SEQ ID NO:5) and/or
N N D E W I Y G E P D S S N I (SEQ ID NO:6) and/or
M N N (X) C E V N C E (X) T and/or
N A S L T W G K (SEQ ID NO:8) and/or
F E L and/or
Q W V K (SEQ ID NO:9) and/or
E N T A S G T E (SEQ ID NO:10) and/or
I E Y H N N L R (SEQ ID NO:11) and/or
A Y (R) Q W V K F H I E A V N E G L K I (SEQ ID NO:12) and/or
D I P I S P E D I S K. (SEQ ID NO.13)

The identification of the amino acid sequences is carried out by having recourse to the single-letter code for designating amino acids.

The invention also relates to a nucleotide fragment contained in one of the sequences defined above, characterized by the following properties:
it comprises the XbaI-EcoRV fragment of the 7 kb XbaI fragment represented in FIG. 4A and contained in the plasmid pCMB1 deposited at CNCM under the No. I-1317,
it has a size of about 1.8 kb and it encodes a protein having a molecular weight of 66 kDa.

A preferred nucleotide fragment encoding a 66 kDa protein is characterized in that it contains a sequence encoding the amino acid chain M N T N I F S T N L at its NH$_2$ terminal end, and a sequence encoding the amino acid chain N N D E W I Y G E P D S S N I as internal fragment (SEQ ID NO:5,6).

Another nucleotide fragment according to the invention, which is contained in one of the sequences defined above, is characterized by the following properties:

it hybridizes under stringent conditions with the probe 16A;
it is present in the 7 kb XbaI fragment represented in FIG. 4A and contained in the plasmid pCMB1 deposited at CNCM under the No. I-1317;
it has a size of about 0.5 kb;
it encodes a protein P16 having a molecular weight of about 16 kDa.

A preferred fragment encoding a protein having a molecular weight of about 16 kDa (protein P16) is, in addition, characterized in that it contains a sequence encoding the amino acid chain A Y (R) Q W V K F H I E A V N E G L K I at its NH$_2$-terminal end and a sequence encoding the amino acid chain D I P I S P E D I S K as internal fragment (SEQ ID NO:12,13).

Another nucleotide fragment according to the invention, which is contained in one of the preceding sequences, is characterized in that it encodes a protein P20 having a molecular weight of about 20 kDa, which is a precursor of the protein P16, P20 being synthesized during the sporulating phase of bacteria of the species *C. bifermentans*, in particular of *Cbm*.

The subject of the invention is also a nucleotide fragment contained in one of the preceding sequences, characterized by the following properties:
it hybridizes under stringent conditions with the probe 18A;
it is present in the 7 kb XbaI fragment represented in FIG. 4A and contained in the plasmid pCMB1 deposited at CNCM under the No. I-1317;
it has a size of about 0.55 kb;
it encodes a protein P18 having a molecular weight of about 18 kDa.

Such a fragment may be preferably characterized in that it encodes a protein having a molecular weight of about 18 kDa and in that it contains a sequence encoding the amino acid chain M N N (X) C E V N C E (X) T at its NH$_2$-terminal end and sequences encoding the amino acid chains N A S L T W G K, F E L, Q W V K, E N T A S G T E, and I E Y H N N L R as internal fragments (SEQ ID NO:7,8,11).

Also forming part of the invention are recombinant vectors characterized in that they contain a nucleotide sequence or a nucleotide fragment corresponding to the preceding definitions, this sequence or this fragment being inserted at a site which is not essential for the replication of the vector. Advantageously, these vectors are plasmids.

A specific vector is characterized in that it is the plasmid pCBM1 deposited at CNCM under the No. I-1317.

Another recombinant vector according to the invention is the plasmid pHT316 which results from the introduction into the plasmid pHT315 (Arantes and Lereclus, 1991, Gene, 108: 115–119) of a 0.5 kb BamHI-EcoRI fragment (Nicolas et al (1993) FEMS Microbiol. Letter 106, 275–280) containing the promoter for *B. thuringiensis* cytolysin (Ward and Ellar, 1986, J. Mol. Biol., 191:1–11). This vector can be modified by the Cbm sequence.

The plasmid pHT316 allows advantageously the overproduction in *Bt* of the *Cbm* proteins which are toxic against insects.

The subject of the invention is also prokaryotic or eukaryotic recombinant host cells, characterized in that they contain a sequence or a fragment corresponding to one of the definitions given above, or a vector of the invention under conditions which allow the cloning and/or the expression of the said sequence or of the said fragment.

A specific host may be a bacterial cell, for example a strain of *Clostridium bifermentans*, a strain of *Bacillus thuringiensis* or a strain of *Bacillus sphaericus*.

As regards *B. thuringiensis*, reference may be made to the publication by Lereclus D. et al (1989), FEMS Microbiology Letters 60, 211–218, in which the technique for transforming (by introducing toxin genes into *Bt*) *B. thuringiensis* is described.

As regards *B. sphaericus*, reference may be made for example to the publication by Taylor L. D. et al (1990) FEMS Microbiology Letters 66, 125–128.

Another cell according to the invention may be an eukaryotic cell, for example a plant cell.

The subject of the invention is also a polypeptide or a polypeptide composition, characterized in that it is encoded by a nucleotide sequence or a nucleotide fragment defined above.

A specific polypeptide according to the invention is involved in a larvicidal activity against the larvae of Diptera, especially of mosquitoes or of simuliids, and is characterized by the following properties:

it is characteristic of an anaerobic bacterium of the species *Clostridium bifermentans*;

it does not produce an immunological reaction with sera directed against the crystal proteins of *B. thuringiensis israelensis* or of *B. sphaericus*.

The polypeptides of the invention comprise especially a first protein characterized in that it has a molecular weight of about 16 kDa and in that it is the product of the expression, in a recombinant cell of a nucleotide fragment which hybridizes with the oligonucleotide 16A under stringent conditions, this fragment being contained in the NsiI-XbaI sequence of the XbaI fragment contained in the plasmid pCMB1 deposited at CNCM under the number I-1317.

Another protein of the invention is characterized in that it has a molecular weight of about 18 kDa and in that the product of the expression, in a recombinant cell, of a nucleotide fragment which hybridizes with the oligonucleotide 18A under stringent conditions, this fragment being contained in the EcoRI-XbaI sequence of the XbaI fragment contained in the plasmid pCMB1 deposited at CNCM under the number I-1317 and described in FIG. 4A.

A third protein according to the invention is characterized in that it has a molecular weight of about 66 kDa and in that it is the product of the expression, in a recombinant cell, of a nucleotide fragment which hybridizes with the oligonucleotide 66A and/or 66B under stringent conditions, this fragment being contained in the XbaI-EcoRI sequence of the XbaI fragment contained in the plasmid pCMB1 deposited at CNCM under the number I-1317.

The invention also relates to the polypeptide fragments of the proteins P16, P18 or P66, or any fragment as obtained from the proteins defined above provided that it is involved in a larvicidal activity against the larvae of Diptera, especially of mosquitoes or of simuliids.

Especially entering within the framework of the invention are the polypeptide sequences encoded by the nucleotide sequences Seq1, Seq2.1, Seq2.2, Seq3 or Seq4 (SEQ ID NOS:26, 27, 28, 29 and 30, respectively.

Another sequence of interest is the amino acid sequence corresponding to the cbm11 gene, as represented in FIG. 6.

According to another embodiment of the invention, a polypeptide of the invention is characterized in that it is recognized by antibodies directed against the protein P16 and/or by antibodies directed against the protein P18 and/or by antibodies directed against the protein P66.

Specific polypeptides of the invention are for example polypeptides comprising an amino acid sequence encoded by one of the chains Seq1, Seq2.1, or Seq2.2 or Seq3 and which are recognized respectively by anti-protein P66 antibodies for the polypeptide comprising at least one of the sequences Seq1, Seq2.1 or Seq2.2 and by anti-protein P16 or anti-protein P18 antibodies for the polypeptide comprising the sequence Seq3.

The application also relates to a polypeptide characterized in that it is modified by addition, deletion, substitution of amino acids provided that it retains the capacity of the corresponding unmodified polypeptide to become involved in the toxic activity against the larvae of Diptera, especially of mosquitoes or of simuliids.

The present application also relates to polypeptide compositions characterized in that they comprise for example the protein P16 and the protein P18 or in that they comprise the proteins P16, P18 and P66.

These proteins are preferably in a form which is purified, where appropriate copurified, either after isolation from a strain, or after expression in a recombinant cellular host.

The invention also relates to a protein extract having a larvicidal activity against the larvae of Diptera, especially of mosquitoes or of simuliids as obtained by:

culturing *Clostridium bifermentans* at 34° C. under anaerobic conditions in TYG medium in a gaseous stream containing 5% $H_2$, 5° $CO_2$ and 90% $N_2$, recovering the culture at the end of sporulation, after about 16 h, washing the culture with 1M NaCl, rinsing twice with a TE buffer, recovering the pellet which constitutes the extract.

A specific polypeptide composition according to the invention may also be characterized in that it has the larvicidal activity of a crude extract as defined above.

The subject of the present application is also monoclonal antibodies directed against a protein according to the definitions given above.

It also relates to a polyclonal antiserum characterized in that it is directed against a protein of the invention or against a composition of these proteins or even against an extract as described above.

The nucleotide sequences or fragments according to the invention also allow the preparation of nucleotide probes obtained by labeling, according to conventional techniques, the fragments or sequences described above.

Also entering within the framework of the invention are compositions with larvicidal activity comprising, as active ingredient, one or more polypeptides according to any one of the definitions given above.

Other compositions with larvicidal activity according to the invention may also be characterized in that they comprise, as active ingredient, recombinant cells corresponding to the definitions given above.

Such compositions may, in addition, contain recombinant cells modified by sequences encoding one or more polypeptides with larvicidal activity of *B. thuringiensis* and/or of *B. sphaericus*.

It can also be envisaged, according to the invention, preparing recombinant cells containing at the same time genes or nucleotide sequences or fragments encoding a protein corresponding to the definitions above and containing, in addition, a sequence with larvicidal activity of *B. thuringiensis* and/or of *B. sphaericus*.

Other characteristics and advantages of the invention appear in the examples and the figures which follow.

BRIEF DESCRIPTION OF THE FIGURES

FIG. 1: SDS-PAGE of the toxic extract of Cbm. The molecular weights of standard proteins are indicated in the right hand margin (in kDa).

FIG. 2: Detection of the proteins P66, P18 and P16 in Cbm and in nontoxic C. bifermentans strains. 100 µl samples of sporulating cultures were subjected to polyacrylamide gel electrophoresis (SDS-PAGE), transferred onto a nitrocellulose membrane and subjected to immunodetection with affinity-purified IgG's directed against P66 (A66), P18 (A18) or P16 (A16). Well a, Cbm; well b, strain ATCC 638; well c, strain 744–83; well d, strain VPI 4407; well e, strain VPI 4413A.

FIG. 3: Kinetics of synthesis of P66, P18 and P16 during sporulation of Cbm, at 34° C. (top) or at 42° C. (bottom), under anaerobic conditions. 100 µl aliquots of culture were subjected to polyacrylamide gel electrophoresis (SDS-PAGE), transferred onto a nitrocellulose membrane and subjected to immunodetection with affinity-purified IgG's directed against P66 (A66), P18 (A18) or P16 (A16). Culture time in hours: a, 4.5; b, 6 (corresponding to $t_0$ of sporulation); c, 7.5; d, 9; e, 10.5; f, 13; g, 30. The molecular weights of standard proteins are indicated in the margin (in kDa).

FIG. 7: Amino acid sequence corresponding to the Cbm11 gene and location of the $NH_2$-terminal and internal sequences of the proteins P18 and P16 (SEQ ID NO:31).

FIGS 11A, 11B and 11C: Sequence homologies found between the protein Cbm 11 and the proteins described in the Swissprot data bank (SEQ ID NO:31–36).

MATERIALS AND METHODS

Preparation of the extract

Figure 1:
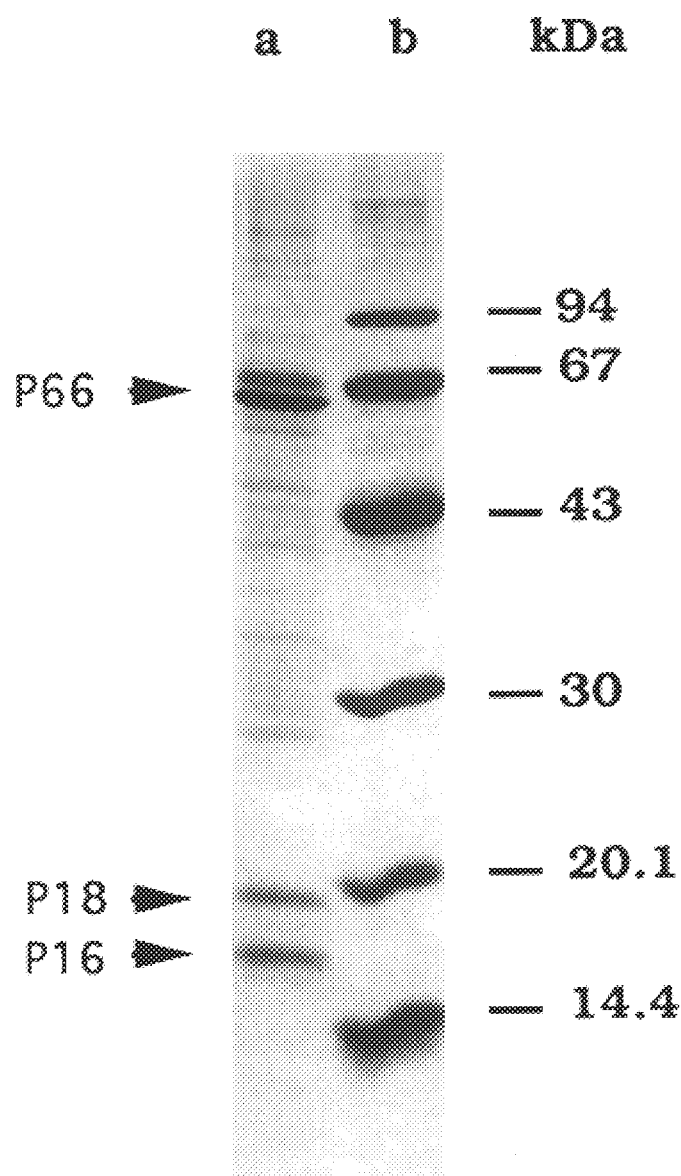
FIGS. 1 to 3: Immunological relationships, distribution and kinetics of synthesis of P66, P18 and P16.

An extract was prepared from a Cbm culture obtained at 34° C. under anaerobic conditions in TYG medium (based on 3% Biotrypcase, 2% yeast extract, 0.5 to 1% glucose, 0.05% cysteine hydrochloride) in a fermenter having a capacity of 6 liters, in the presence of a gaseous stream containing 5% $H_2$, 5% $CO_2$ and 90% $N_2$. The sporulating bacterial culture was harvested after 16 h, at the end of the sporulating phase. The culture was then washed with 1M NaCl, rinsed twice with 20 mM Tris HCl, 5 mM EDTA, pH8 (TE buffer) and stored at −70° C. up to the time of use. The frozen pellets were thawed, resuspended in a TE buffer, treated in a sonicator for a total period of 1 minute comprising a real sonication time of 15 seconds on ice (Branson sonicator, large probe, outlet scale 40%, duration of the sonication cycle ("duty cycle": 25%) and centrifuged at 5000 g for 15 min. The resulting supernatant (corresponding to the crude protein extract) was recovered.

Protein analysis

The protein concentration of the extract was determined using the Biorad protein test with bovine serum albumin as standard. A polyacrylamide gel electrophoresis was carried out according to the technique of Laemmli, U.K. (1970) (Nature 227, 680–685) on 13% polyacrylamide gels. The molecular weight markers used in this SDS-PAGE protein analysis under denaturing conditions are those of the Pharmacia protein electrophoresis kit (LMW Ref. 17-0446-01), containing the following proteins: phosphorylase B (with a molecular mass of 94,000 daltons), albumin (67,000), ovalbumin (43,000), anhydrase (30,000) trypsin inhibitor (20, 100) and alpha lactalbumin (14,000).

Preparation of antisera against the Cbm proteins

Polyclonal antisera against the crude Cbm protein extract were obtained in rabbits after two series of 10 to 15 intradermal microinjections of 500 µg of protein emulsified in complete Freund's adjuvant, at an interval of 3 weeks. The rabbits received subcutaneous injections of a booster dose without Freund's adjuvant, 3 weeks later. The IgG's were purified from the sera by ammonium sulfate precipitation and chromatography on a DEAE-52 column (Whatmann) and then stored at 4° C.

Polyclonal antisera against the denatured individualized polypeptides P66, P18 and P16 were produced in rabbits in the following manner: three proteins were separated by preparative SDS-PAGE electrophoresis and detected with 1M KCl. The bands were cut out from the gels and the acrylamide bands cut out were rinsed with deionized water, and then immersed in water, emulsified with complete Freund's adjuvant and injected into the rabbits according to the technique described above. After recovering the antisera, the IgG's were affinity-purified on nitrocellulose bands containing the polypeptide used for the injection into rabbits, according to the technique of Burke et al (1982). EMBO J. 1, 1621–1628.

Enzymatic hydrolysis of the Cbm extract

In order to evaluate the toxicity of the extract, 500 µl of aliquots of the extract (400 µg) were each treated for two hours at 37° C. with one of the following enzymes: proteinase K (EC 3.4.21.14, Boehringer, 40 µg/ml), ribonuclease type I-A (EC 3.1.27.5, Sigma, 100 µg/ml) and deoxyribonuclease I (EC 3.1.21.1, Boehringer, 100 µg/ml).

The larvicidal activity was tested on *Anopheles stephensi* larvae at the third larval instar.

Fractionation of the protein extract

The crude protein extracts were filtered on an HA-MILLEX filter containing pores of 0.45 µm (millipore) and subjected to a high-resolution liquid chromatography (FPLC®, Pharmacia). An ion-exchange chromatography was carried out on a MONO Q HR 10/10 column equilibrated with a TE buffer. The proteins were eluted with a multi-step gradient containing from 0 to 1M NaCl. A gel filtration was carried out on a SUPERDEX 200 HILOAD 16/60 column in a TE buffer containing 150 mM NaCl (TES buffer). The fractions were analyzed by electrophoresis (SDS-PAGE) after precipitation of the proteins with 10% trichloroacetic acid.

Neutralization and immunoprecipitation tests

The capacity of the various antisera to inhibit the larvicidal activity of the extract was tested according to the following method: serial dilutions of the extract were incubated with a fixed volume of antiextract IgG in a TE buffer at 20° C. for 1 hour. The toxicity of the samples and of the untreated control samples was tested using *A. stephensi* larvae. Neutralization tests were also carried out under the same conditions with the antisera or the affinity-purified antibodies, directed against the denatured proteins P66, P18 or P16. The proteins were immunoprecipitated from the extract with the antisera directed against the extract or against the denatured individual proteins P66, P18 or P16 by the technique of Howe et al, ((1982). Mol. Gen. Genet. 186, 525–530), using Protein A SEPHAROSE beads (Sigma) as carrier.

Kinetics of the synthesis of P66. P18 and P16

*Cbm* was grown in 1 liter sealed bottles containing 800 ml of liquid TYG medium, with gentle magnetic stirring, either at 34° C. or at 42° C. 30 ml samples were recovered at 90-minute intervals without renewing the gas content by piercing through a rubber stopper. The samples were centrifuged, rinsed as described above and the centrifugation pellets were kept at −70° C. up to the analysis of the larvicidal activity and of the protein content by SDS-PAGE electrophoresis. The immunodetection experiments were carried out after electrotransfer onto a HYBOND-C SUPER® membrane (Amersham). P66, P18 and P16 were detected with the affinity-purified IgG's directed against each protein (A66, A18 and A16) and visualized with an ECL® Western blot detection system (Amersham). For comparison, the cultures were carried out at 34° C. and 42° C. in bottles in which gas exchange was possible.

Screening of P66. P18 and P16 in nonlarvicidal *C. bifermentans* strains

The nonlarvicidal strains of *C. bifermentans* (type strain ATCC 638, 744–83, VPI 4407 and VPI 4413A were screened by immunodetection in order to search for the presence of P66, P18 and P16. These strains, as well as the *Cbm* strain, were cultured in sealed bottles containing 50 ml of TYG medium, at 34° C. and recovered after 15 h when the sporulation was completely over but before the cell lysis.

Bioassays on mosquito larvae

Samples of bacterial culture or of the protein extracts were tested on 20 larvae of *Culex pipiens* at the fourth larval instar and/or of *A. stephensi* at the third larval instar in plastic Petri dishes with a capacity of 6 ml. The mortality was recorded after 24 h and 48 h of exposure.

Immunological relationships with Bacillus toxins

A crude *Cbm* extract was tested with antisera directed against the crystals from *B. thuringiensis* serovar *israelensis* 1884, *B. thuringiensis* serovar *aizawai* 7.29, *B. thuringiensis* serovar *thuringiensis* 1715 and *B. thuringiensis* serovar *entomocidus* HD9, as well as antisera against the 42 and 51 kDa crystal proteins from *B. sphaericus* 2362.

RESULTS AND DISCUSSION

Figure 2:
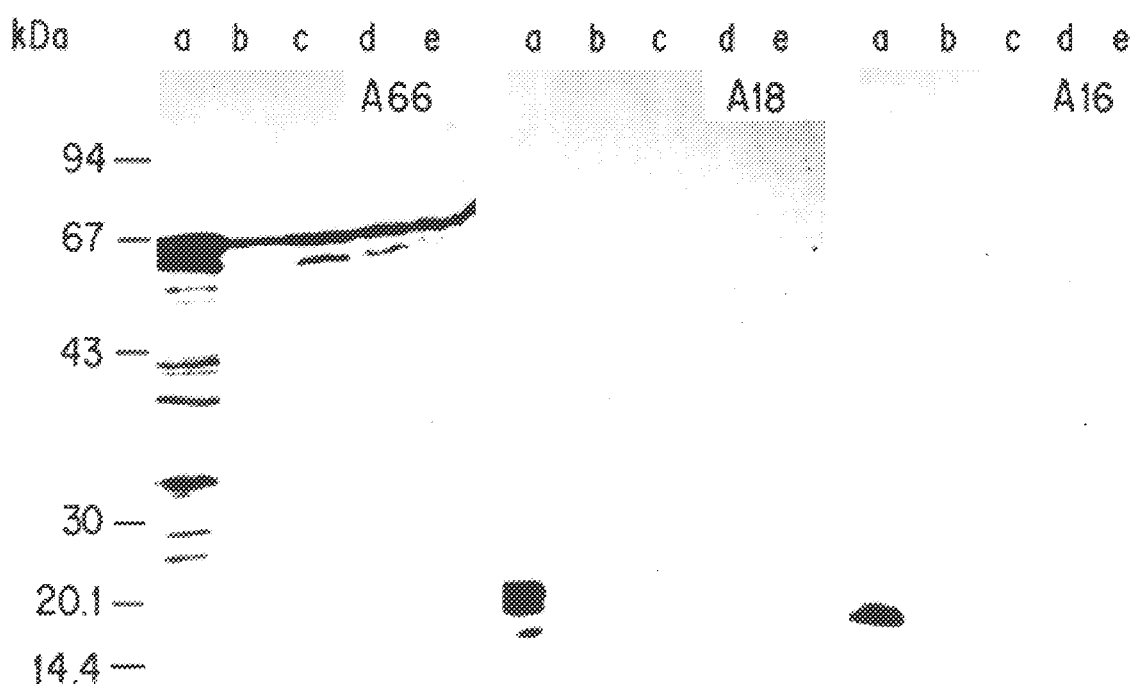
Figure 3:
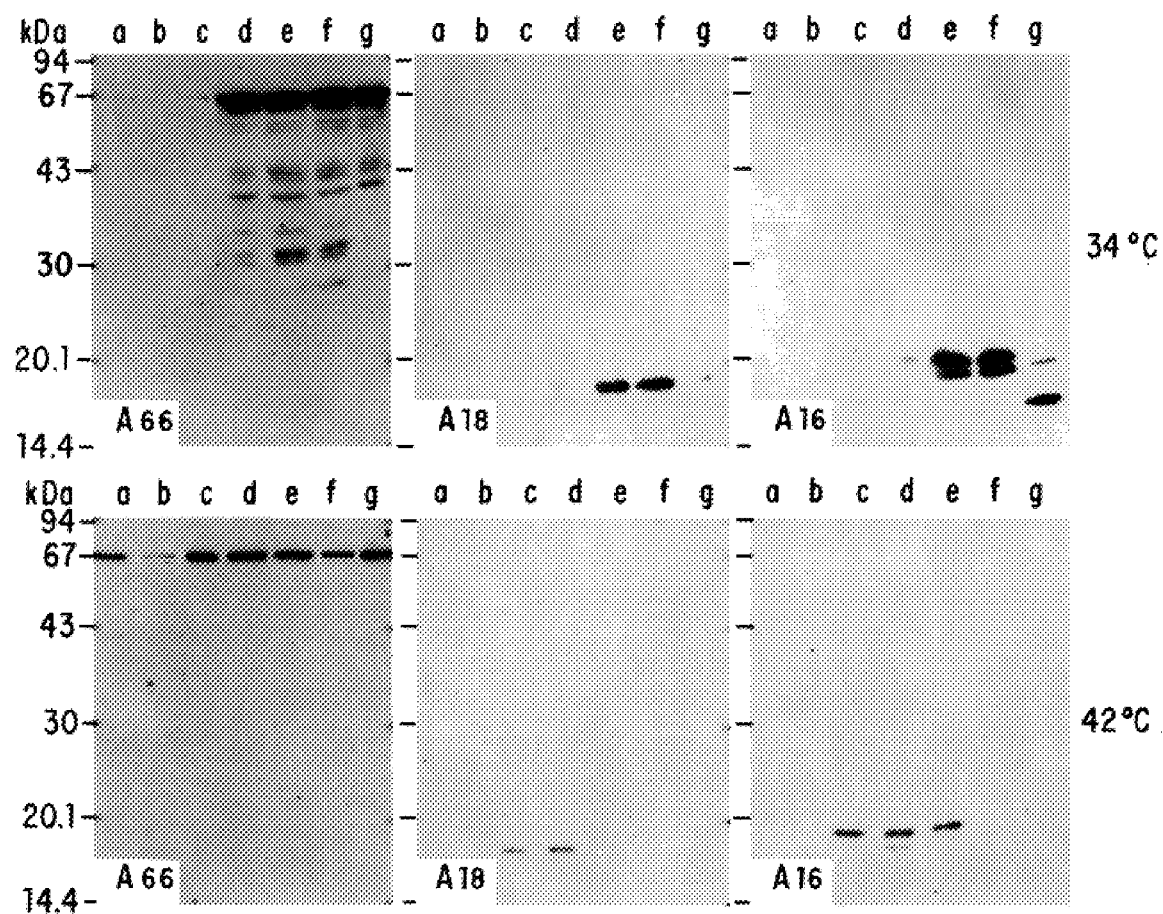

The *Cbm* extract contained three major proteins with apparent molecular weights of 66, 18 and 16 kDa, designated by the abbreviations P66, P18 and P16,as well as various minor components of protein nature (FIGS. 1 to 3).

1. Characterization of the P66, P18 and P16 proteins

The extract obtained is toxic toward the larvae of the mosquitoes *Culex pipiens, Anopheles stephensi* and *Aedes aegypti.*

Its $LC_{50}$ after 48 h against *A. stephensi* at the third larval instar was 5 µg/ml. The larvicidal activity of the extract was lost after incubating for 2 h at 37° C. with proteinase K. In contrast, no inactivation was obtained with DNase or RNase. Furthermore, the larvicidal activity was completely inhibited by the IgG's directed against the total extract. Thus, the larvicidal activity is indeed due to toxins of a protein nature, at least in part.

Antisera directed against the entomopathogenic crystal proteins from *B. thuringiensis* or *B. sphaericus* did not give rise to a cross-reaction with the proteins of the *Cbm* extract, indicating that the *Cbm* toxins belong to a new class of insecticidal toxins.

P66, P18 and P16 are the predominant components of the toxic *Cbm* extracts.

P66, P18 or P16 are not immunlogically related (FIG. 2, lines a). P18 and P16 were only present in *Cbm* whereas a 66 kDa protein immunologically related to Cbm P66 was detected in 4 strains of nonentomopathogenic strains of *C. bifermentans* tested (FIG. 2, lines b to e).

The synthesis of P18 and P16 in a culture carried out at 34° C. was concomitant with the sporulation of *Cbm* (FIG. 3) and the appearance of the larvicidal activity. P16 was synthesized in the form of a 20 kDa precursor (P20) which was gradually converted to a 16 kDa polypeptide during the cell lysis (FIG. 3).

P18 and P20/P16 are not immunologically detected in the strains of *C. bifermentans* lacking larvicidal activity (FIG. 2).

P18 and P20/P16 are very weakly detected in *Cbm* cultured at 42° C., under conditions where the bacterium is not toxic (FIG. 3).

P66 was detected in *Cbm* cells during the vegetative stage and during sporulation. In the sporulating cells, other polypeptides immunologically related to P66 were detected, ranging from 25 to 66 kDa (FIG. 3); these polypeptides could be products of the degradation of P66.

The *Cbm* culture grew at 42° C. without gaseous exchange; it was not toxic and contained only traces of P18 and P16. In this culture, P66 was also synthesized during the vegetative phase but no protein of a lower molecular weight was detected (FIG. 3). In the cultures with gaseous exchange, no difference was noted in the larvicidal activity, the synthesis of P66, P18 and P16 and the lysis of the sporangium, between the cultures carried out at 34° C. or at 42° C.

Trials for the purification of each protein allowed the following observations to be made: most of the toxicity was lost after filtration, before carrying out an FPLC® chromatography, although the filtered and nonfiltered extracts had the same protein profiles. This suggests that the larvicidal activity could be linked to the presence of protein aggregates or particles. This was also observed for the *Bti* or *B. sphaericus* toxins which are much more active in the form of aggregates than in solution (Schnell et al (1984). Science 223, 1191–1193 and Nicolas et al (1993). FEMS Lett. 106, 275–280). In addition, with FPLC® chromatography, either on an ion-exchange column, or by gel filtration, the three polypeptides P66, P18 and P16 coeluted at different points. Immunoprecipitation tests have shown that each of the individual antisera directed against P66, P18 or P16 were capable of precipitating the three products together as was the case with antibodies prepared against the crude extract. Chromatography and immunoprecipitation tests suggested that P66, P18 and P16 are assembled into a complex.

IgG's directed against the denatured proteins P66, P18 and/or P16 did not neutralize the toxicity; on the other hand, the denatured proteins were capable of recognizing the P66-P18-P16 complex, but did not recognize epitopes or domains involved in the larvicidal activity.

These experiments showed the involvement of P18 and P16 in the larvicidal activity. Indeed, in *Cbm* cultures carried out at 34° C., both proteins are synthesized concomitantly with the appearance of the larvicidal activity. They are absent from nontoxic strains of *C. bifermentans* and are present at a very low level in nontoxic *Cbm* cells cultured at 42° C. The larvicidal activity of *Cbm* at 42° C. is modulated by the conditions for gas exchange between the culture and the mixture of anaerobic gas. The absence of larvicidal activity in sealed bottles, without gaseous exchange, is correlated with the low synthesis and/or a rapid degradation of P18 and P20/P16.

2. Cloning of the genes encoding P66, P18 and P16

Partial amino acid sequences of P66, P18 and P16 were determined by microsequencing.

Amino acid sequences of the proteins P66, P18 and P16

These sequences were obtained by micro-sequencing, according to techniques commonly used by microsequencing laboratories. The following were obtained for each protein: i) the $NH_2$-terminal sequences and ii) one or more sequences of internal fragments obtained by trypsin hydrolysis of the protein. The sequences were determined with an Applied Biosystems 470 sequencer using the proteins separated on SDS-PAGE and transferred onto a PVDF IMMOBILON membrane (millipore).

| | |
|---|---|
| p66 | |
| -$NH_2$-terminal sequence M N T N I F S T N L (complete sequence: SEQ ID NO: 5, underlined portion: SEQ ID NO:22) | |
| -internal 1 (complete sequence: SEQ ID NO:6, underlined portion: SEQ ID NO:23) | N N D E W I Y G E P D S S N I |
| p18 | |
| -$NH_2$-terminal (complete sequence: SEQ ID NO:7, underlined portion: SEQ ID NO:24) | M N N (X) C E V N C E (X) T |
| -internal 1 (SEQ ID NO:8) | N A S L T W G K |
| -internal 2 | F E L |
| -internal 3 (SEQ ID NO:9) | Q W V K |
| -internal 4 (SEQ ID NO:10) | E N T A S G T E |
| -internal 25 (SEQ ID NO:11) | I E Y H N N L R |
| P16 | |
| -$NH_2$-terminal (complete sequence: SEQ ID NO:12; underlined sequence: SEQ ID NO:25) | A Y (R) Q W V K F H I E A V N E G L K I |
| -internal 1 (SEQ ID NO:13) | D I P I S P E D I S K |

(X):not determined antibodies against the crude fraction of the extract neutralized the toxicity. It is conceivable that IgG's directed against The oligonucleotide probes were made from the sequences underlined

| Protein | Amino acids | Oligonucleotide probe 5'–3' |
|---|---|---|
| P66, $NH_2$-term. (SEQ ID NO:22) | M N T N I F S T N | 66A (SEQ ID NO:3) = ATG AAT ACI AAT ATI TTT TCI ACI AA (26 mer) |
| P66, internal | D E W I Y G E P D | 66B (SEQ ID NO:4) = TC IGG TTC ICC ATA IAT CCA TTC ATC (26 mer) |
| P18, $NH_2$-term. (SEQ ID NO:24) | C E V N C E | 18A (SEQ ID NO:2) = TGT GAA GTI ATT TGT GA (17 mer) |
| P16, $NH_2$-term. | F H I E A V N E G | 16A (SEQ ID NO:1) = TTT CAT ATI GAA |

-continued

| Protein | Amino acids | Oligonucleotide probe 5'–3' |
|---------|-------------|------------------------------|
| (SEQ ID NO:25) | | GCI GTI AAT GAA GG (26 mer) |

I = DMT dInosine cyanoethyl phosphoramidite
* = complementary sequence

From this information, oligonucleotide probes were synthesized and used to screen a *Cbm* XbaI enzyme-hydrolyzed total DNA library constructed in the shuttle plasmid pHT304 (Arantès & Lereclus, Gene. 1991. 108:115–119).

Selection of the plasmid pCBM1

Figure 5:
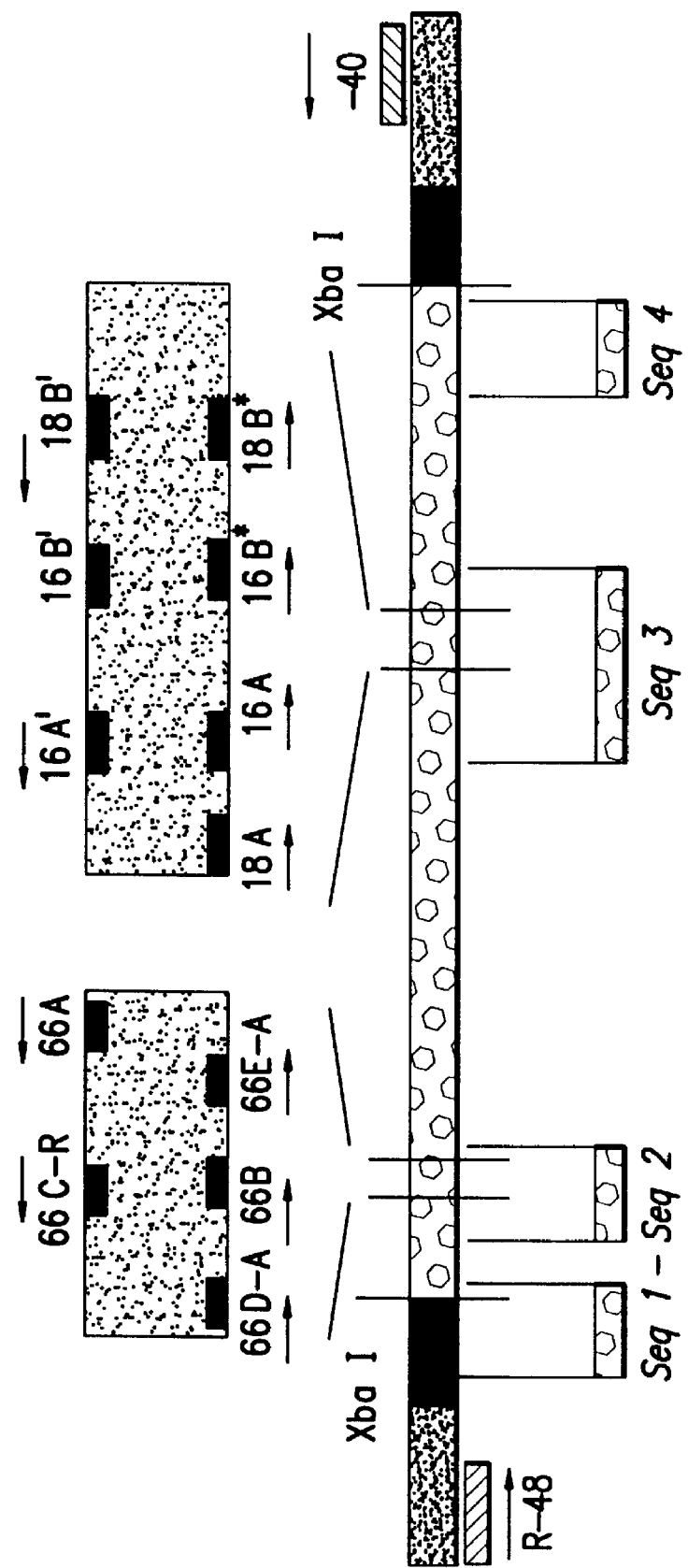
FIG. 5: Location of the oligonucleotides used for the sequencing of the sequences read.
Sequences of the oligonucleotides used (SEQ ID NOS:14–21):
16A': complementary 16A:: acc cat tgt cta tat gc
16B*: nondegenerate oligon 16B: ggagat atc gga atg tc
16B': complementary 16B'*: ccg ata tct cct gaa ga
18B: nondegenerate oligo 18B: tct gta ccg gaa gca gt
18B': complementary 18b*: gct tcc ggt aca gaa gg
66C-R: aac cct aca tct gtt aa
66D-A: tac tac cat agt ttc ca
66E-A: tgc aaa gcc aag ttg at
Legend
XbaI fragment inserted, derived from the Cbm DNA
"Reverse" primer R-48
"Universal" primer—40
pUC 19 polylinker
Synthetic nucleotide primers (*)
Shuttle vector pHT 304
Figure 6A:
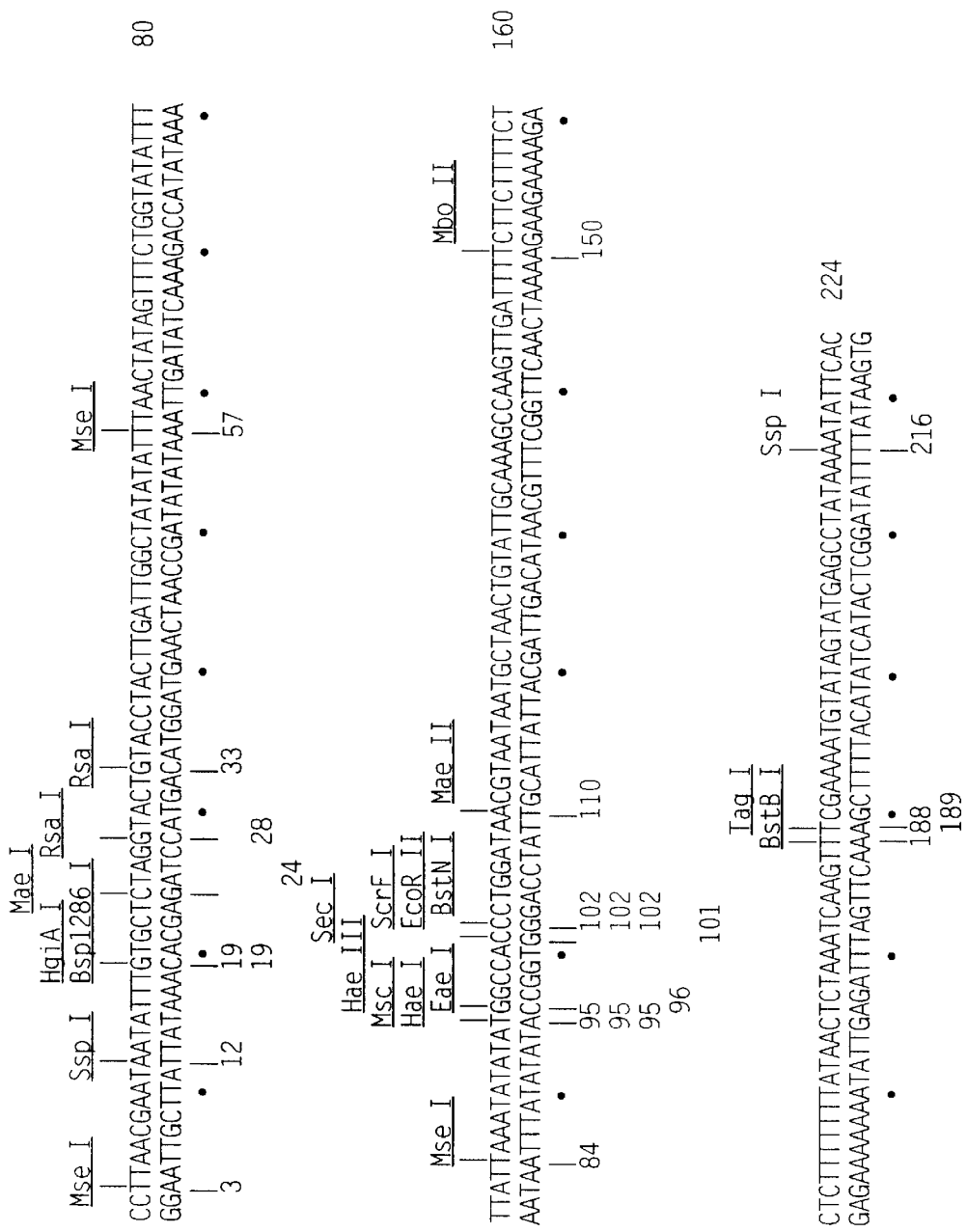
FIG. 6: Nucleotide sequences read.
6A:Seq.1, read with the aid of the reverse primer R-48 (SEQ ID NO:26).
6B: Seq.2.1, read with the aid of the primer 66C-R (SEQ ID NO:27).
6C and 6D: Seq.2.2, read with the primers 66B, 66D-A and 66E-A (SEQ ID NO:28).
6E to 6G: Cbm gene, read with the various primers "16 and 18" (SEQ ID NO:29).
6H to 6J: SEq4, read with the universal primer R-40 (SEQ ID NO:30).
Figure 6B:
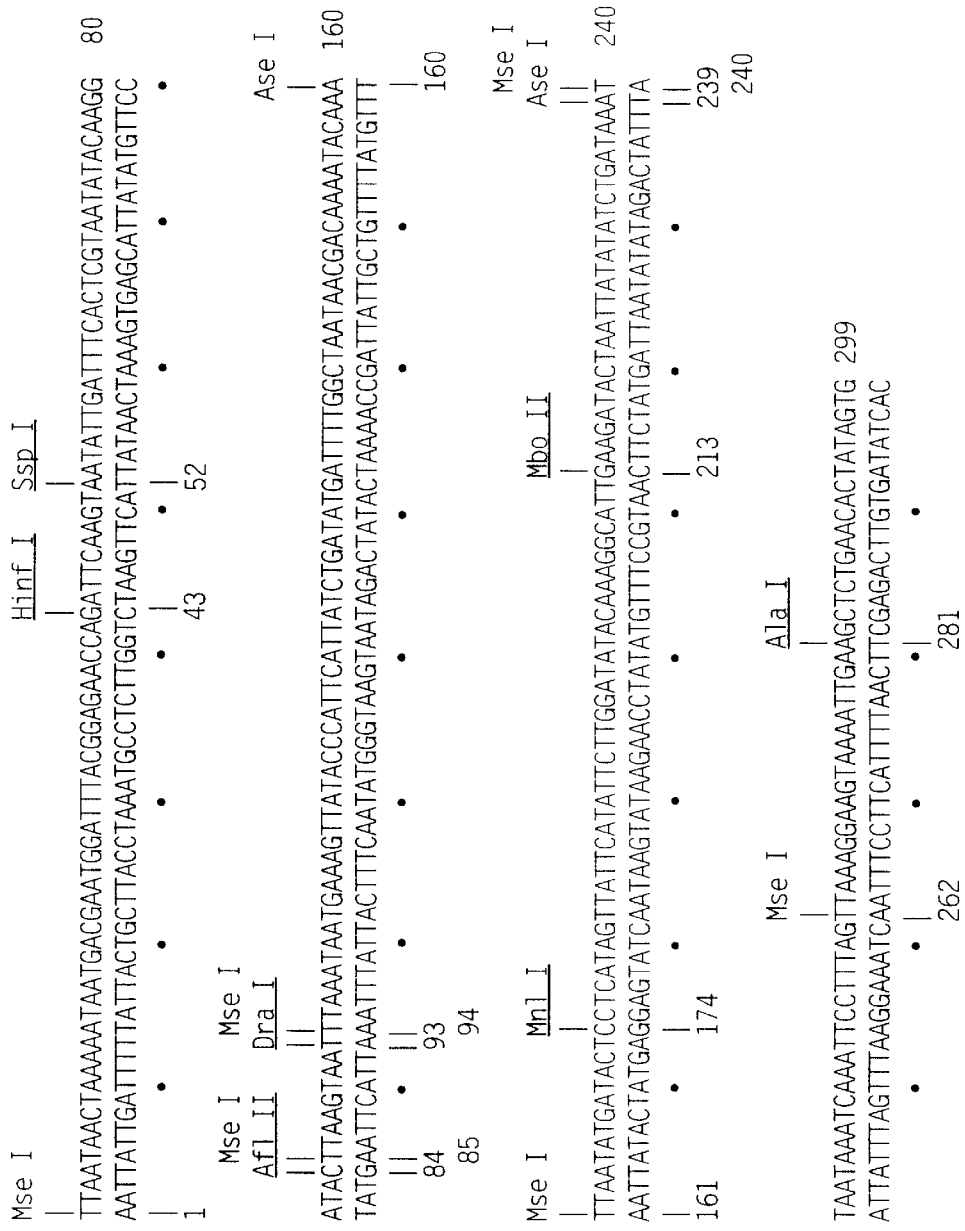
Figure 6C:
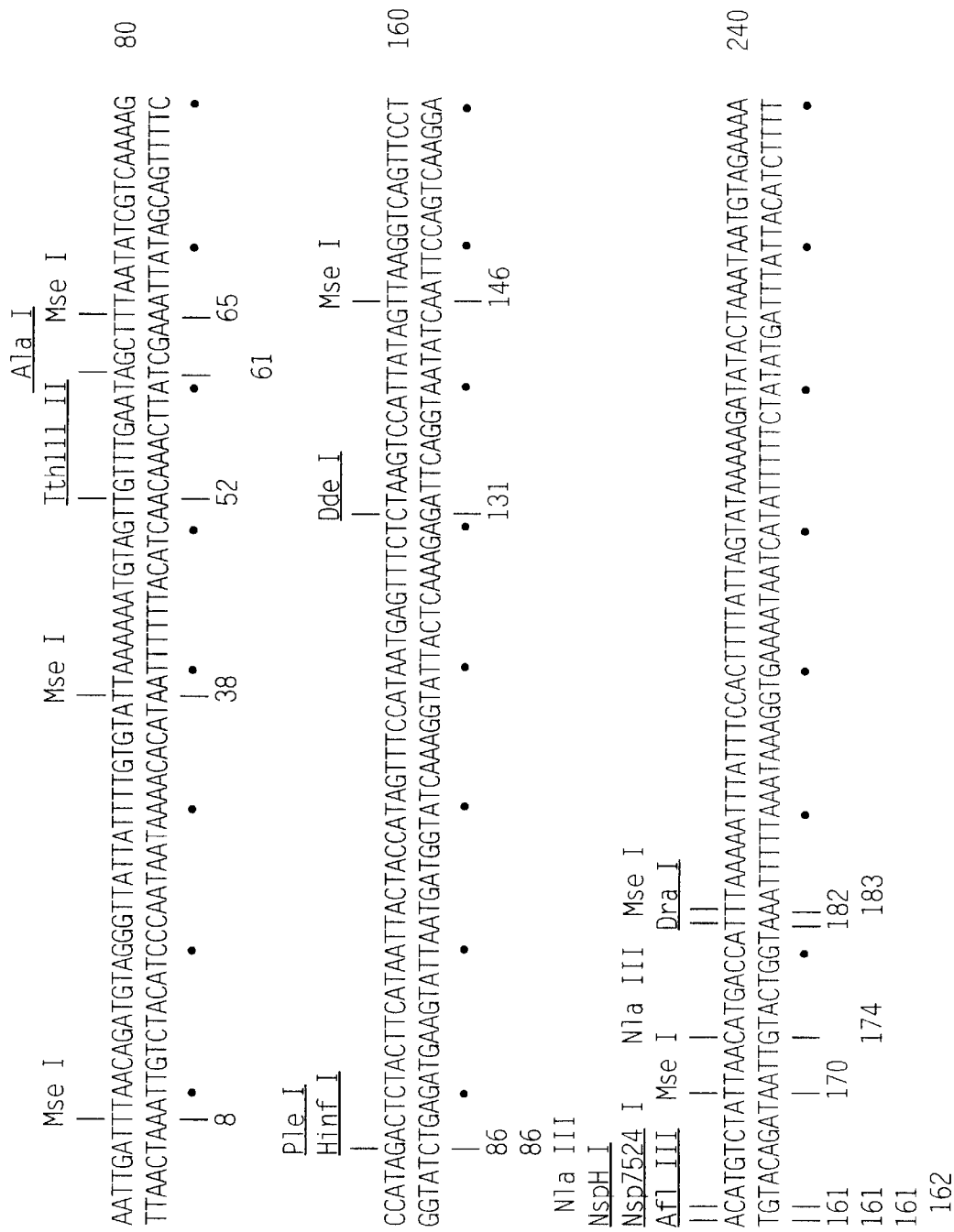
Figure 6E:
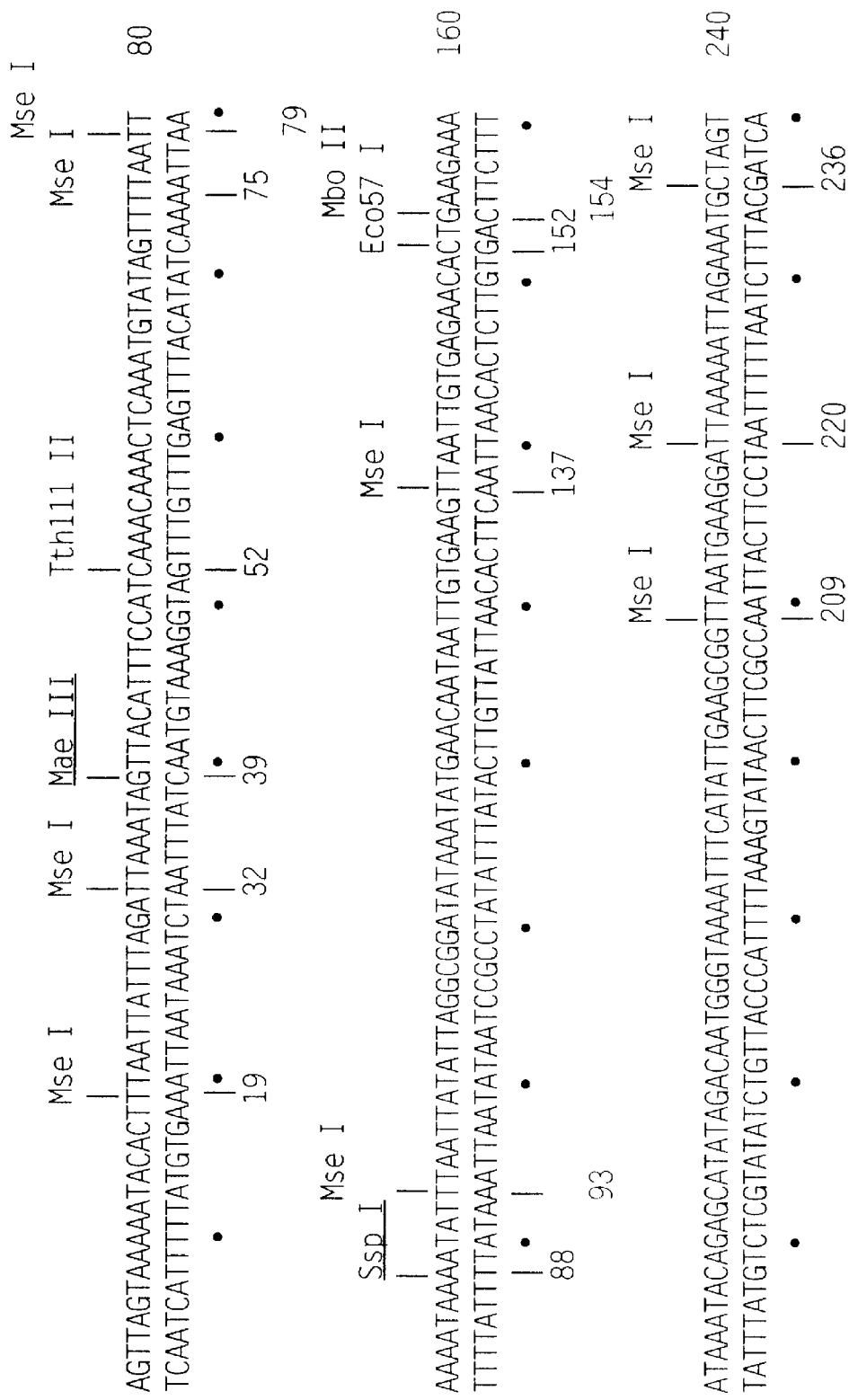
Figure 6F:
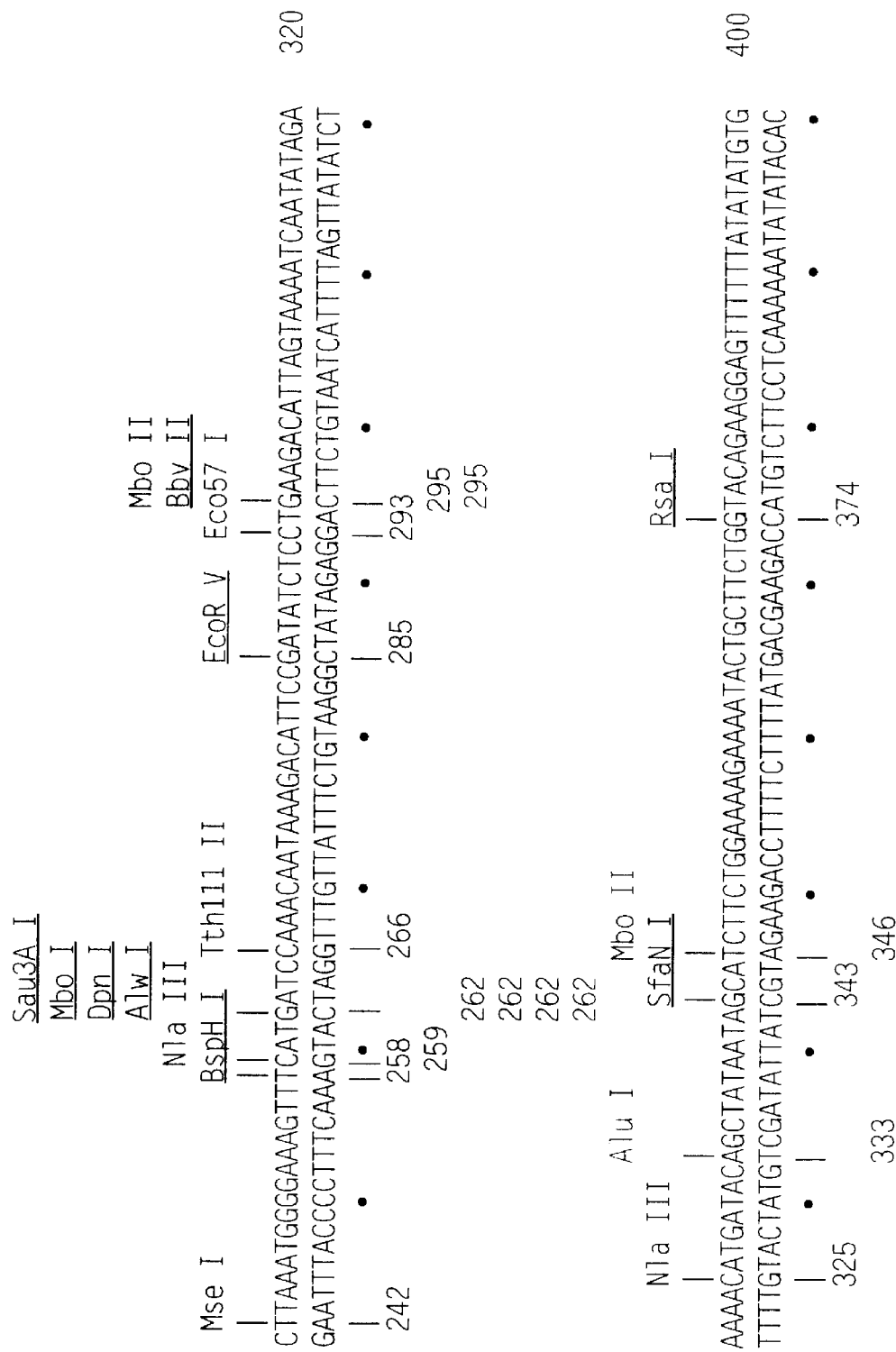
Figure 6G:
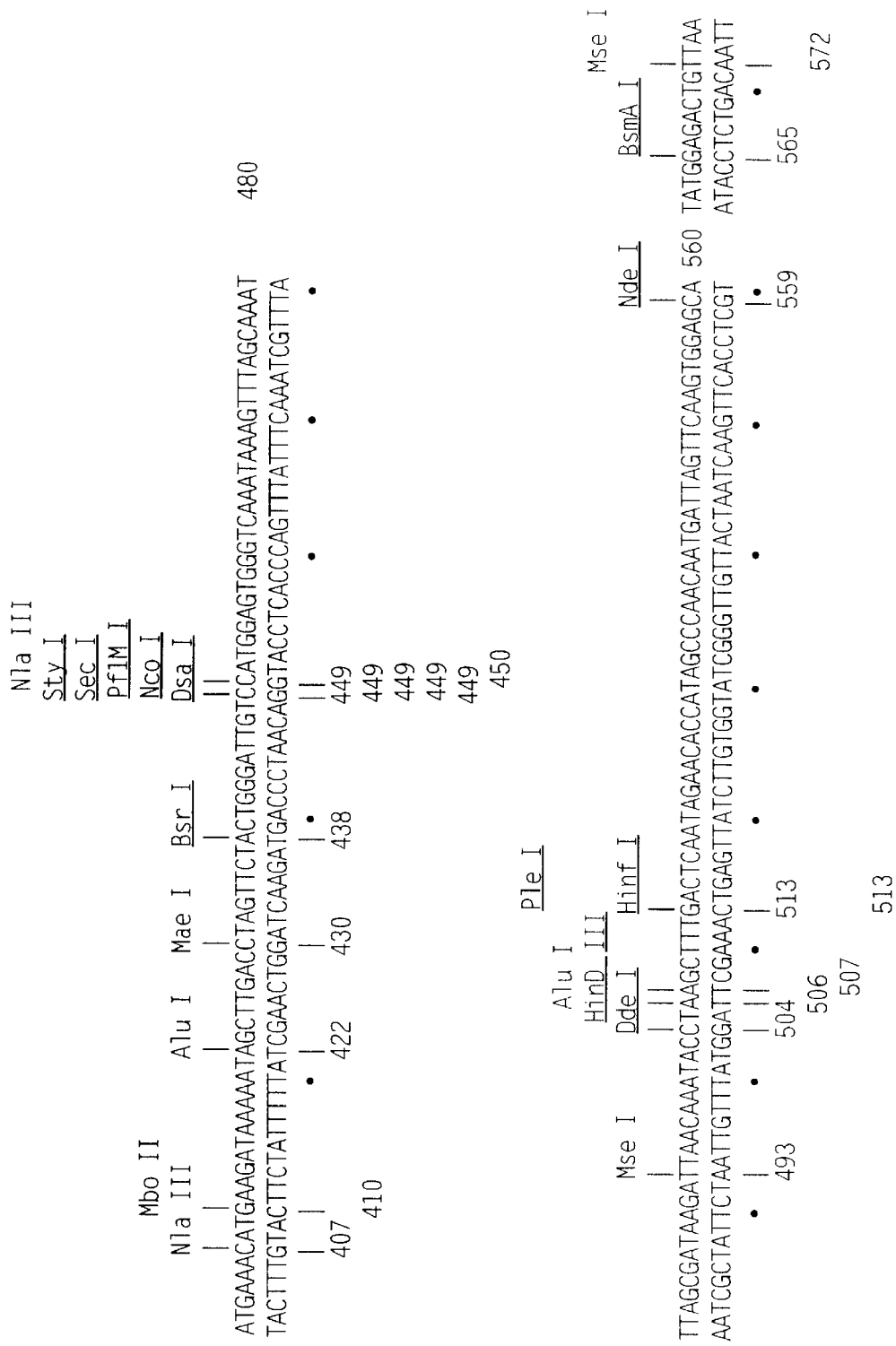
Figure 6I:
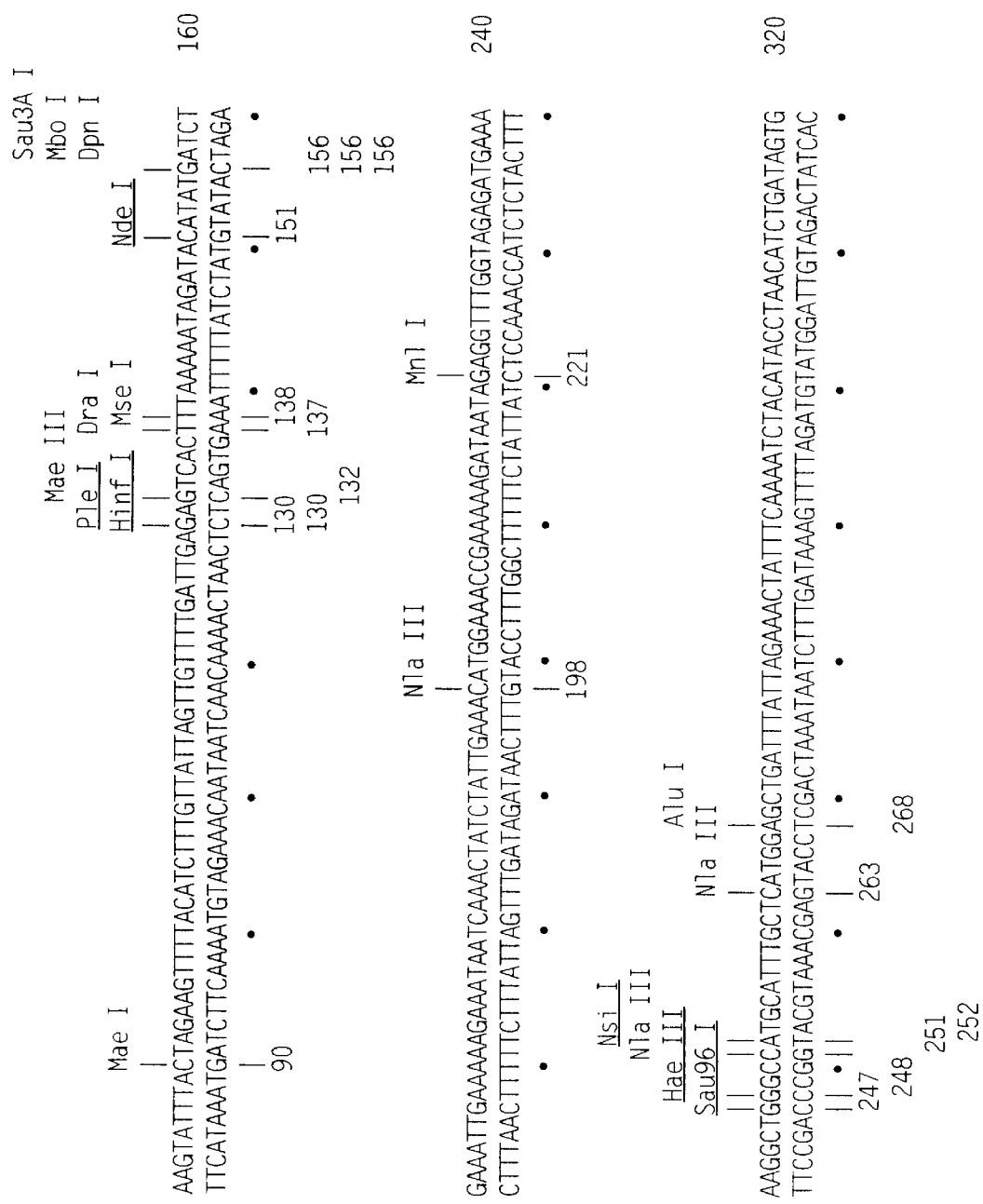
Figure 8:
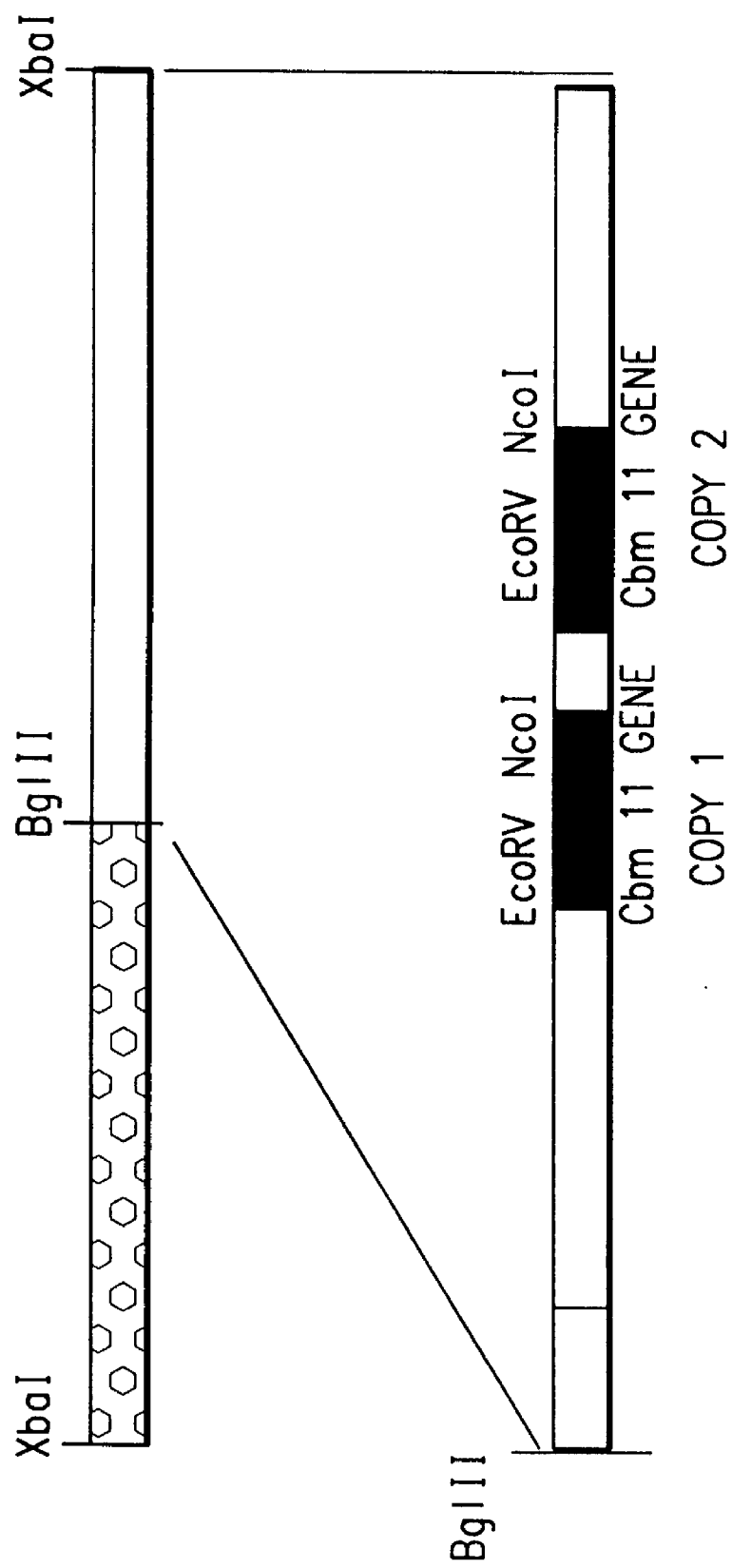
FIG. 8: Location of the copies of cbm 11 on the XbaI fragment.
Figure 9A:
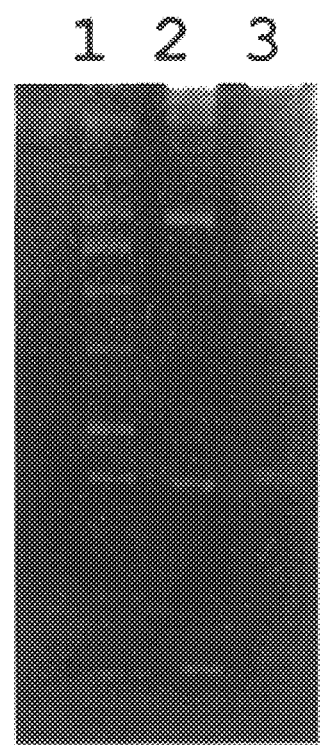
FIG. 9A and 9B: Location of the XbaI fragment on the resident plasmid.
Line 1: Size marker CCC from 16 to 2.06 Kb
Line 2: Preparation of the native Cbm CH 18 plasmids
Line 3: Preparation of the XbaI-hydrolyzed Cbm CH 18 plasmids hydrolyzed with Xba
Probe used: pCBM1
Figure 9B:
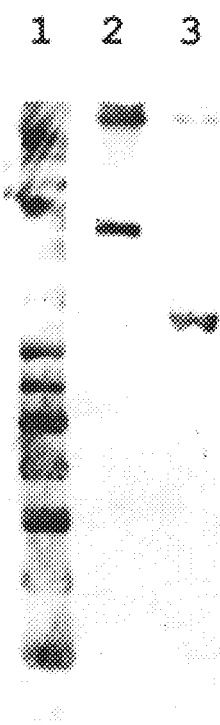
Figure 10:
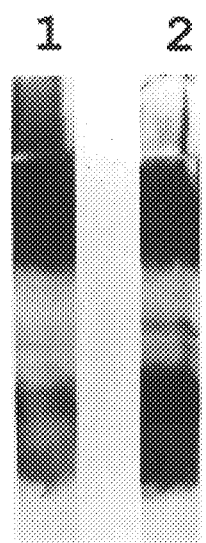
FIG. 10: Expression of the genes introduced into pCBM1, in E.coli
Line 1: E.coli+pHT 304 (shuttle vector used)
Line 2: E.coli+pCBM 1
Probe used: total anti-Cbm antibody.

A DNA library was constructed in a shuttle vector pHT304, constructed by O. Arantès and D. Lereclus, from a *B. thuringiensis* resident plasmid pHT 1030 and from pUC19, which is capable of replicating in *E. coli* and in Gram-positive bacteria. The *Cbm* total DNA was hydrolyzed with XbaI, transferred onto a HYBOND N+ membrane (Amersham) after agarose gel electrophoresis, and hybridized with each of the probes synthesized, labeled at the 3' end with fluorescein ("kit ECLT™ 3' oligolabeling and detection systems", Amersham) according to the procedure recommended by the supplier under the following hybridization and stringency conditions:

Hybridization temperature: 42° C., 15 h, in a HYBAID hybridization oven (Cera-Labo) with 5–10 ng of probes/ml.

Washes after hybridization: twice 5 minutes at room temperature in 5×SSC, 0.1% SDS, then twice 15 minutes in 1×SSC, 0.1% SDS.

The *Cbm* genomic DNA library constructed in *E. coli* strain TG1 was screened by colony hybridization with the oligonucleotide 16A labeled at the 3' end with fluorescein (ECL 3' oligolabeling system Amersham). The screening made it possible to isolate a recombinant plasmid pCBM1 which hybridizes with the oligonucleotide 16A but also with the oligonucleotides 66A, 66B and 18A.

A single 7 kb band was detected on the DNA hydrolyzed with XbaI with the probe corresponding to the $NH_2$-terminal end of P16 (probe 16A) . A weak reaction was also detected on this fragment with the probes 18A and 66A. The library was therefore constructed in *E. coli* TG1 with the XbaI fragments of DNA having a size of close to 7.5 kb which are eluted on PREP-A-GENE (Biorad). The screening of the library (400 clones) by colony hybridization on a HYBOND N+ filter with the oligonucleotide 16A revealed 10 positive clones (same stringency conditions as described above). Analysis of the 10 recombinant plasmids, with several restriction enzymes, showed that they were all similar. One of the plasmids (pCBM1, 13.5 kb) was selected.

The plasmid pCBM1 has a size of 13.5 kb and therefore results from the insertion of a 7 kb XbaI fragment of DNA of *Cbm* at the XbaI cloning site of pHT304 (6.5 kb).

The restriction map of pCBM1 was determined (FIG. 4A and 4B).

The regions with which the abovementioned probes hybridize were determined by Southern blotting on the plasmid pCBM1 hydrolyzed with various restriction enzymes for the 4 probes. Furthermore, the PCR technique, using as primers, the universal primer and the oligonucleotide 16A, made it possible to locate the region for hybridization of 16A at 2 kb from the 3' end of the XbaI fragment (FIG. 4A) . These results make it possible to conclude that the 3 genes encoding P66, P20/16 and P18 are contained in the 7 kb XbaI fragment.

PCR location of the 5' end of the gene encoding P16 on the XbaI fragment

A PCR was carried out using Taq polymerase and, as primers, the oligonucleotide 16A and the universal primer (M13 universal sequencing primer Pharmacia) and, as template, the plasmid pCBM1, with the following cycle:

| | | | |
|---|---|---|---|
| 1 cycle | Denaturation: | 95° C. | 10 min. |
| 25 cycles | Hybridization: | 42° C. | 1 min. |
| | Extension: | 72° C. | 2 min. |
| | Denaturation: | 95° C. | 1 min. |
| 1 cycle | Hybridization: | 42° C. | 3 min. |
| | Extension: | 72° C. | 4 min. |

3. Determination of the nucleotide sequence

The sequencing strategy used was that of "fragment walking". The sequence was established according to the technique of Sanger (Sanger et al., 1977, Proc. Natl. Acad. Sci. USA, 74:5463–5467) on the plasmid pCBM1 rendered single-stranded by denaturation with sodium hydroxide. The extension was performed using reverse, universal primers, or the oligonucleotides corresponding to the sequences deduced from the amino acid sequences of the proteins P66, P18 and P16 or the nucleotide sequences read. All the oligonucleotides used and their location on the DNA fragment are represented in FIG. 5.

A total of 1800 bp was read and is represented in FIG. 6. The nucleotide sequences (Seq1, Seq2, Seq3 and Seq4) determined, as well as the amino acid sequence deduced from the sequence Seq3 are given in FIG. 6.

The determination of the restriction sites contained in the sequence of the gene encoding the 66 kDa protein made it possible to locate precisely the position of the beginning of the 66 kDa gene on the XbaI fragment; about 95% of the gene is present on the cloned fragment.

Analysis of the sequence Seq3 and comparison with the terminal and internal amino sequences of the 16 kDa and 18 kDa proteins (mentioned in FIG. 6) showed that the 16 kDa and 18 kDa genes are not different and in fact represent the same gene. A single reading frame capable of encoding an 11 kDa (calculated molecular mass) protein was found; the corresponding gene was designated CBM11 gene. The calculated molecular mass of 11 kDa is thought to correspond to that of the 18 kDa protein. According to the sequence, the 16 kDa protein is in fact thought to be a protein having a calculated molecular mass of 8.9 kDa; it is thought to result from the 11 kDa protein by cleavage of the 17 $NH_2$-terminal amino acids.

The search for homologies at the amino acid level between the Seq3 sequence and other proteins was carried out. Only three proteins (including one produced by another Clostridium species) having very limited homologies were found in the data banks.

The existence of a single gene encoding the two proteins is in apparent contradiction with a result previously found regarding the absence of an immunological relationship between these proteins. A search was therefore carried out for the presence of several copies of the CBM 11 gene encoding different proteins.

4. Copy number of the CBM 11 gene PCR experiments carried out on the plasmid pCBM1 with various combinations of primers described in FIG. 5 showed the presence of two copies of the *Cbm* 11 gene on the 7 kb XbaI fragment cloned. These two copies have similar sizes, are in a direct orientation and are separated by about 200 bp (FIG. 8).

Similar experiments carried out on the total *Cbm* DNA made it possible to show the existence of at least one additional copy on this DNA in a reverse orientation.

5. Location of the genes encoding the 66 kDa. 18 kDa and 16 kDa proteins

Hybridization experiments were carried out in parallel on the plasmid DNA and total DNA of *Cbm* using, as probe, the 7 kb XbaI fragment; these experiments were carried out using the cold probe ECL "Direct nucleic acid labelling system" technique (Amersham), according to the supplier's information. The results obtained made it possible to locate this fragment on a resident plasmid of about 13 kb (FIG. 9A and 9B).

6. Expression of the genes for the 66 kDa. 18 kDa and 16 kDa proteins in E. coli The study of the expression of the genes cloned into the plasmid pCBM1 was carried out in *E.coli* by immunodetection using cold probes. The *E.coli* extracts were prepared in the following manner: the clones TG1 (pHT304 ) and TG1 (pCBM1) were cultured in LB medium. This experiment demonstrated the synthesis in this recombinant of a single protein of 20 kDa which reacts specifically with the anti-18 kDa protein antibody (FIG. 10). No product corresponding to the expression of the 66 kDa gene was able to be visualized.

Biological tests carried out on *Anopheles stephensi* Liston show that this recombinant clone, although synthesizing a protein which is immunologically related to the *Cbm* proteins, exhibits no toxicity even at a high concentration. This suggests that the 20 kDa protein expressed in *E.coli* is not the only component responsible for the toxicity of *Cbm* and confirms the results obtained regarding a phenomenon of synergism between the various proteins produced by *Cbm*.

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OLIGONUCLEOTIDE"

( x i ) SEQUENCE DESCRIPTION: SEQ ID NO:1:

TGTGAAGTNA ATTGTGA 17

( 2 ) INFORMATION FOR SEQ ID NO:2:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OLIGONUCLEOTIDE"

( x i ) SEQUENCE DESCRIPTION: SEQ ID NO:2:

TTTCATATNG AAGCNGTNAA TGAAGG 26

( 2 ) INFORMATION FOR SEQ ID NO:3:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OLIGONUCLEOTIDE"

( x i ) SEQUENCE DESCRIPTION: SEQ ID NO:3:

ATGAATACNA ATATNTTTTC NACNAA 26

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONULCEOTIDE"

( x i ) SEQUENCE DESCRIPTION: SEQ ID NO:4:

TCNGGTTCNC CATANATCCA TTCATC      26

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Met Asn Thr Asn Ile Phe Ser Thr Asn Leu
1            5                  10

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Asn Asn Asp Glu Trp Ile Tyr Gly Glu Pro Asp Ser Ser Asn Ile
1                5                     10                    15

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Met Asn Asn Xaa Cys Glu Val Asn Cys Glu Xaa Thr
1                5                     10

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Asn Ala Ser Leu Thr Trp Gly Lys
1                5

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Gln  Trp  Val  Lys
   1

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Glu  Asn  Thr  Ala  Ser  Gly  Thr  Glu
   1                          5

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Ile  Glu  Tyr  His  Asn  Asn  Leu  Arg
   1                          5

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Ala  Tyr  Arg  Gln  Trp  Val  Lys  Phe  His  Ile  Glu  Ala  Val  Asn  Glu  Gly
   1                     5                        10                      15

Leu  Lys  Ile ( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Asp Ile Pro Ile Ser Pro Glu Asp Ile Ser Lys
 1               5                   10
```

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE,
            COMPLEMENTARY TO SEQ ID NO:2"

( x i ) SEQUENCE DESCRIPTION: SEQ ID NO:14:

```
ACCCATTGTC TATATGC                                                                17
```

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONULCEOTIDE,
            NON- DEGENERATE OLIGONUCLEOTIDE 16 B"

( x i ) SEQUENCE DESCRIPTION: SEQ ID NO:15:

```
GGAGATATCG GAATGTC                                                                17
```

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE,
            COMPLEMENTARY 16 B'*'"

( x i ) SEQUENCE DESCRIPTION: SEQ ID NO:16:

```
CCGATATCTC CTGAAGA                                                                17
```

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE,
            NON- DEGENERATE OLIGO 18 B"

( x i ) SEQUENCE DESCRIPTION: SEQ ID NO:17:

```
TCTGTACCGG AAGCAGT                                                                17
```

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
   ( A ) DESCRIPTION: /desc = "OLIGONUCLEOTIDE"

( x i ) SEQUENCE DESCRIPTION: SEQ ID NO:18:

GCTTCCGGTA CAGAAGG                                                17

( 2 ) INFORMATION FOR SEQ ID NO:19:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "OLIGONUCLEOTIDE"

( x i ) SEQUENCE DESCRIPTION: SEQ ID NO:19:

AACCCTACAT CTGTTAA                                                17

( 2 ) INFORMATION FOR SEQ ID NO:20:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "OLIGONULCEOTIDE"

( x i ) SEQUENCE DESCRIPTION: SEQ ID NO:20:

TACTACCATA GTTTCCA                                                17

( 2 ) INFORMATION FOR SEQ ID NO:21:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "OLIGONUCLEOTIDE"

( x i ) SEQUENCE DESCRIPTION: SEQ ID NO:21:

TGCAAAGCCA AGTTGAT                                                17

( 2 ) INFORMATION FOR SEQ ID NO:22:

( i ) SEQUENCE CHARACTERISTICS:
       ( A ) LENGTH: 9 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:22:

Met Asn Thr Asn Ile Phe Ser Thr Asn
   1               5

( 2 ) INFORMATION FOR SEQ ID NO:23:

( i ) SEQUENCE CHARACTERISTICS:
       ( A ) LENGTH: 9 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:23:

Asp Glu Trp Ile Tyr Gly Glu Pro Asp
1               5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

Cys Glu Val Asn Cys Glu
1               5

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Phe His Ile Glu Ala Val Asn Glu Gly
1               5

( 2 ) INFORMATION FOR SEQ ID NO:26:

( i ) SEQUENCE CHARACTERISTICS:
        ( A ) LENGTH: 224 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

```
CCTTAACGAA TAATATTTGT GCTCTAGGTA CTGTACCTAC TTGATTGGCT ATATATTTAA      60
CTATAGTTTC TGGTATATTT TTATTAAATA TATATGGCCA CCCTGGATAA CGTAATAATG     120
CTAACTGTAT TGCAAAGCCA AGTTGATTTT CTTCTTTTCT CTCTTTTTTT ATAACTCTAA     180
ATCAAGTTTC GAAAATGTAT AGTATGAGCC TATAAAATAT TCAC                      224
```

( 2 ) INFORMATION FOR SEQ ID NO:27:

( i ) SEQUENCE CHARACTERISTICS:
        ( A ) LENGTH: 299 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:27:

```
TTAATAACTA AAAATAATGA CGAATGGATT TACGGAGAAC CAGATTCAAG TAATATTGAT      60
TTCACTCGTA ATATACAAGG ATACTTAAGT AATTTAAATA ATGAAAGTTA TACCCATTCA     120
TTATCTGATA TGATTTTGGC TAATAACGAC AAAATACAAA TTAATATGAT ACTCCTCATA     180
GTTATTCATA TTCTTGGATA TACAAAGGCA TTGAAGATAC TAATTATATA TCTGATAAAT     240
```

| TAATAAATCA | AATTCCTTTA | GTTAAAGGAA | GTAAAATTGA | AGCTCTGAAC | ACTATAGTG | 299 |

( 2 ) INFORMATION FOR SEQ ID NO:28:

( i ) SEQUENCE CHARACTERISTICS:
        ( A ) LENGTH: 432 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

| AATTGATTTA | ACAGATGTAG | GGTTATTATT | TTGTGTATTA | AAAAATGTAG | TTGTTTGAAT | 60 |
| AGCTTTAATA | TCGTCAAAAG | CCATAGACTC | TACTTCATAA | TTACTACCAT | AGTTTCCATA | 120 |
| ATGAGTTTCT | CTAAGTCCAT | TATAGTTAAG | GTCAGTTCCT | ACATGTCTAT | TAACATGACC | 180 |
| ATTTAAAAAT | TTATTTCCAC | TTTTATTAGT | ATAAAAGAT | ATACTAAATA | ATGTAGAAAA | 240 |
| AAGTTCTGGA | GAAATATTAT | ACATTTTCTC | ATATCACTAA | TTGGTATATC | TCATCTATAA | 300 |
| ATTTACAGGA | TCTGAATAAA | CTTTTCTTGT | GAGAGTTTGC | ATATTTATAG | GTTTATCATA | 360 |
| TCTTTTGTAT | CATATATTGG | GAAAATAGAA | ATCATGTCTA | GGATGTAAAA | AGTCATAAAT | 420 |
| CTACAATATC | TG | | | | | 432 |

( 2 ) INFORMATION FOR SEQ ID NO:29:

( i ) SEQUENCE CHARACTERISTICS:
        ( A ) LENGTH: 575 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

| AGTTAGTAAA | AATACACTTT | AATTATTTAG | ATTAAATAGT | TACATTTCCA | TCAAACAAAC | 60 |
| TCAAATGTAT | AGTTTTAATT | AAAATAAAAT | ATTTAATTAT | ATTAGGCGGA | TATAAATATG | 120 |
| AACAATAATT | GTGAAGTTAA | TTGTGAGAAC | ACTGAAGAAA | ATAAATACAG | AGCATATAGA | 180 |
| CAATGGGTAA | AATTTCATAT | TGAAGCGGTT | AATGAAGGAT | TAAAATTAG | AAATGCTAGT | 240 |
| CTTAAATGGG | GAAAGTTTCA | TGATCCAAAC | AATAAAGACA | TTCCGATATC | TCCTGAAGAC | 300 |
| ATTAGTAAAA | TCAATATAGA | AAAACATGAT | ACAGCTATAA | TAGCATCTTC | TGGAAAAGAA | 360 |
| AATACTGCTT | CTGGTACAGA | AGGAGTTTTT | TATATATGTG | ATGAAACATG | AAGATAAAAA | 420 |
| TAGCTTGACC | TAGTTCTACT | GGGATTGTCC | ATGGAGTGGG | TCAAATAAAG | TTTAGCAAAT | 480 |
| TTAGCGATAA | GATTAACAAA | TACCTAAGCT | TTGACTCAAT | AGAACACCAT | AGCCCAACAA | 540 |
| TGATTAGTTC | AAGTGGAGCA | TATGGAGACT | GTTAA | | | 575 |

( 2 ) INFORMATION FOR SEQ ID NO:30:

( i ) SEQUENCE CHARACTERISTICS:
        ( A ) LENGTH: 403 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

| GGTTAGTGAA | TTCGAGCTCG | GTACCCGGGG | ATCCTCTAGA | AATTTATTAT | TTTATGGTAT | 60 |

```
TGAAGATGGA   TGCTCTGATA   AAGTATTTAC   TAGAAGTTTT   ACATCTTTGT   TATTAGTTGT        120

TTTGATTGAG   AGTCACTTTA   AAAATAGATA   CATATGATCT   GAAATTGAAA   AAGAAATAAT        180

CAAACTATCT   ATTGAAACAT   GGAAACCGAA   AAAGATAATA   GAGGTTTGGT   AGAGATGAAA        240

AAGGCTGGGC   CATGCATTTG   CTCATGGAGC   TGATTTATTA   GAAACTATTT   CAAAATCTAC        300

ATACCTAACA   TCTGATAGTG   CAACAAGGGT   CACTTTAAAA   ATAGATACAT   AGATACTGAA        360

ATTGAAAAAG   AAATAATCAA   ACATCTATTG   AATACAGGAA   ACC                           403
```

( 2 ) INFORMATION FOR SEQ ID NO:31:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:31:

```
Met  Asn  Asn  Asn  Cys  Glu  Val  Asn  Cys  Glu  Asn  Thr  Glu  Glu  Asn  Lys
1                   5                        10                       15

Tyr  Arg  Ala  Tyr  Arg  Gln  Trp  Val  Lys  Phe  His  Ile  Glu  Ala  Val  Asn
               20                       25                       30

Glu  Gly  Leu  Lys  Ile  Arg  Asn  Ala  Ser  Leu  Lys  Trp  Gly  Lys  Phe  His
               35                       40                       45

Asp  Pro  Asn  Asn  Lys  Asp  Ile  Pro  Ile  Ser  Pro  Glu  Asp  Ile  Ser  Lys
     50                       55                       60

Ile  Asn  Ile  Glu  Lys  His  Asp  Thr  Ala  Ile  Ile  Ala  Ser  Ser  Gly  Lys
65                       70                       75                       80

Glu  Asn  Thr  Ala  Ser  Gly  Thr  Glu  Gly  Val  Phe  Tyr  Ile  Cys  Asp  Glu
               85                       90                       95

Thr
```

( 2 ) INFORMATION FOR SEQ ID NO:32:

( i ) SEQUENCE CHARACTERISTICS:
        ( A ) LENGTH: 100 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

```
Xaa  Ala  Asp  Ile  Asn  Met  Asn  Asn  Asn  Cys  Glu  Val  Asn  Cys  Glu  Asn
1                   5                        10                       15

Thr  Glu  Glu  Asn  Lys  Tyr  Arg  Ala  Tyr  Arg  Gln  Trp  Val  Lys  Phe  His
               20                       25                       30

Ile  Glu  Ala  Val  Asn  Glu  Gly  Leu  Lys  Ile  Arg  Asn  Ala  Ser  Leu  Lys
               35                       40                       45

Trp  Gly  Lys  Phe  His  Asp  Pro  Asn  Asn  Lys  Asp  Ile  Pro  Ile  Ser  Pro
          50                       55                       60

Glu  Asp  Ile  Ser  Lys  Ile  Asn  Ile  Glu  Lys  His  Asp  Thr  Ala  Ile  Ile
65                       70                       75                       80

Ala  Ser  Ser  Gly  Lys  Glu  Asn  Thr  Ala  Ser  Gly  Thr  Glu  Gly  Val  Phe
               85                       90                       95

Tyr  Ile  Cys  Asp
               100
```

( 2 ) INFORMATION FOR SEQ ID NO:33:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:33:

```
Gly Asn Asp Ile Tyr Phe Met Asp Val Leu Glu Val Ile Lys Gly Gly
 1               5                  10                  15
Thr Asp Arg Asn Ala Gln Ala Lys Ala Arg Gln Tyr Val Ser Gln Arg
             20                  25                  30
Lys Cys Gln Glu Ala Leu Asn Leu Lys Leu Asp Asn Asp Tyr Leu Ile
         35                  40                  45
Trp Gly Leu Ser Ser Asp Leu Trp Pro Met Lys Asp Asp Ile Ser Tyr
     50                  55                  60
Leu Ile Thr Lys Asn Thr Trp Ile Glu Arg Trp Pro Asn Glu Asp Glu
 65                  70                  75                  80
Cys Gln Asp Glu Glu Phe Gln Asn Leu Cys Asp Asp Phe Ala Gln Leu
                 85                  90                  95
Ser Asn Thr Leu Thr Ile Phe Gly Cys Pro
            100                 105
```

( 2 ) INFORMATION FOR SEQ ID NO:34:

( i ) SEQUENCE CHARACTERISTICS:
        ( A ) LENGTH: 110 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

```
Asn Asn Thr Asn Asn Asn Asn Asn Asn Thr Asn Asn Asn Thr Asn Asn
 1               5                  10                  15
Asn Asn Asn Asn Ile Asn Asn Asn Asn Asn Thr Asn Asn Asn Asn
             20                  25                  30
Asn Asn Ala Asn Asn Gln Asn Thr Asn Asn Asn Asn Met Gly Asn Asn
         35                  40                  45
Ser Asn Asn Asn Asn Asn Pro Asn Asn Asn Asn His Gln Asn Asn Asn
     50                  55                  60
Asn Asn Asn Thr Ser Asn Asn Ser Asn Thr Thr Thr Ala Thr Thr Thr
 65                  70                  75                  80
Ala Pro Gly Gly Asn Asn Leu Thr Asn Ser Leu Asn Asn Ala Gly Asn
                 85                  90                  95
Leu Gly Asn Leu Gly Arg Val Ser Gly Leu His Ser Ser Asp
            100                 105                 110
```

( 2 ) INFORMATION FOR SEQ ID NO:35:

( i ) SEQUENCE CHARACTERISTICS:
        ( A ) LENGTH: 94 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:35:

-continued

| Asn 1 | Asn | Asn | Cys | Glu 5 | Val | Asn | Cys | Glu | Asn 10 | Thr | Glu | Glu | Asn | Lys 15 | Tyr |
| Arg | Ala | Tyr | Arg 20 | Gln | Trp | Val | Lys | Phe 25 | His | Ile | Glu | Ala | Val 30 | Asn | Glu |
| Gly | Leu | Lys 35 | Ile | Arg | Asn | Ala | Ser 40 | Leu | Lys | Trp | Gly | Lys 45 | Phe | His | Asp |
| Pro | Asn 50 | Asn | Lys | Asp | Ile | Pro 55 | Ile | Ser | Pro | Glu | Asp 60 | Ile | Ser | Lys | Ile |
| Asn 65 | Ile | Glu | Lys | His | Asp 70 | Thr | Ala | Ile | Ile | Ala 75 | Ser | Ser | Gly | Lys | Glu 80 |
| Asn | Thr | Ala | Ser | Gly 85 | Thr | Glu | Gly | Val | Phe 90 | Tyr | Ile | Cys | Asp | | |

Figure 4A:
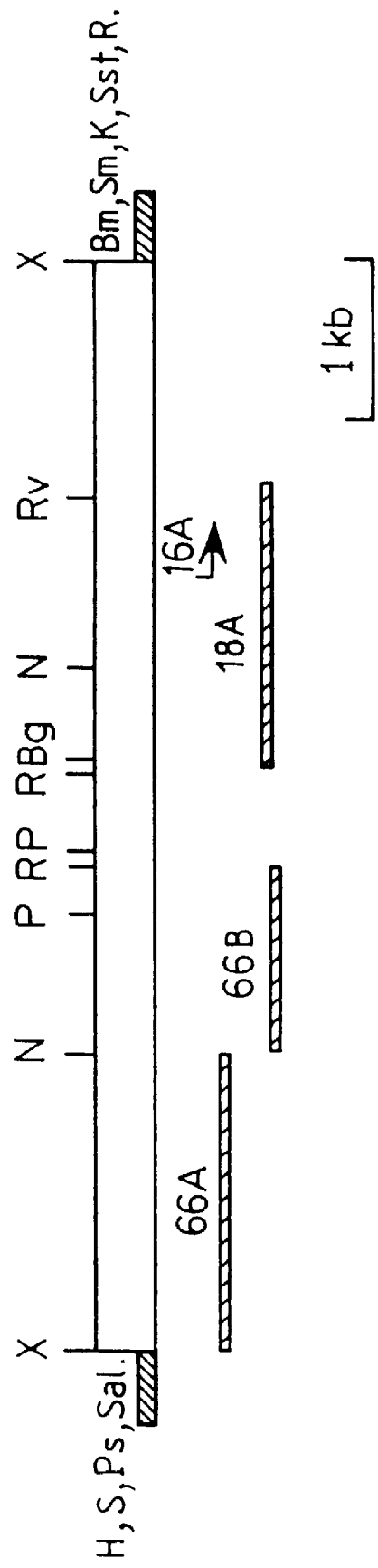
FIGS. 4A and 4B: Structure of the plasmid pCBM1 and restriction map of the XbaI fragment.
XbaI fragment: Bg: BglII; N: NsiI; P: PvuII; R: EcoRI; Rv: EcoRV; X: XbaI
Cloning site:
H: HindIII; S: SphI; Ps: PstI; Sal; SalI; Bm: BamHI; Sm: SmaI; K: KpnI; Sst: SstI; R: EcoRI.
The shaded parts on the right and on the left of the XbaI fragment are fragments of the plasmid vector pHT304 (Arantès O. et al (1991), Gene, 108, p. 115–119).
The fragments to which the oligonucleotide probes hybridize are represented as shaded lines, under the XbaI fragment.
The arrow corresponds to the 5' end of the P16 gene which hybridizes with the probe 16A.
Enzymes not having restriction sites in the XbaI fragment: BaHI, HIndIII, PstI, SstI, SalI, SmaI.
Figure 4B:
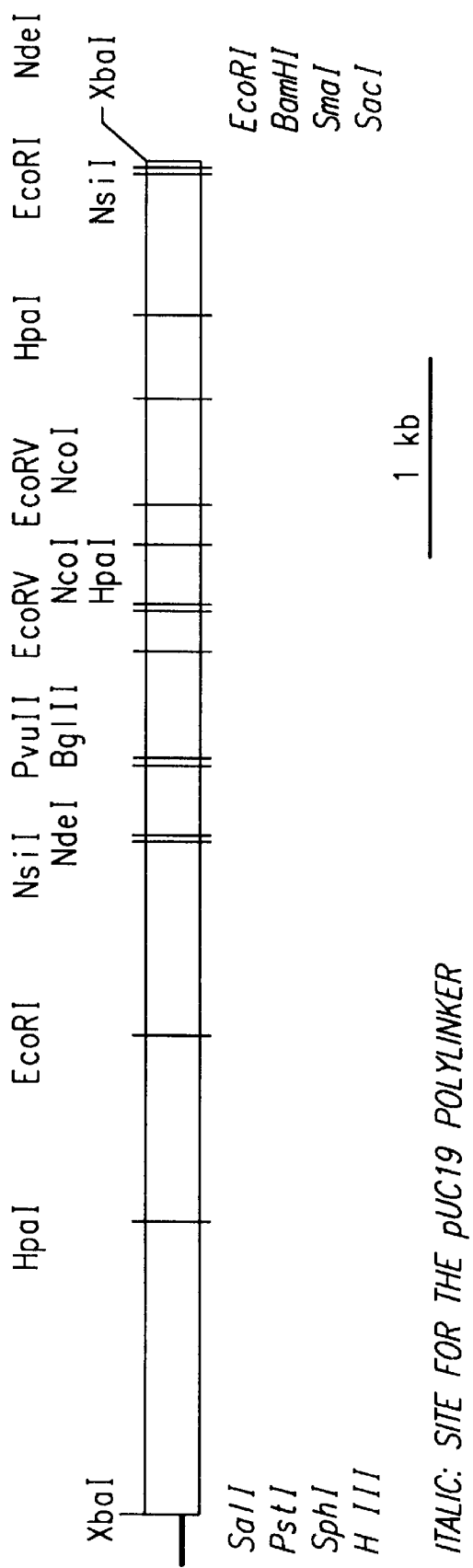

We claim:

1. A nucleotide sequence having the following properties:
said nucleotide sequence comprises a 7 kb Xba I DNA fragment of FIG. 4A or a fragment thereof, obtained from plasmid pCBM1 deposited at CNCM on Jun. 15, 1993 under accession number I-1317;
said nucleotide sequence hybridizes under stringent conditions with an oligonucleotide identified by SEQ ID NO:1, 2, 3 or 4, or a mixture thereof; and
said nucleotide sequence encodes a protein, polypeptide or peptide toxic against Diptera larvae.

2. The nucleotide sequence of claim 1, wherein said Diptera is a mosquito or simuliid.

3. The nucleotide sequence of claim 1, wherein said nucleotide sequence hybridizes with the oligonucleotides identified by SEQ ID NO:1, 2, 3 or 4, or a mixture thereof under stringent conditions.

4. The nucleotide sequence of claim 1, wherein said nucleotide sequence is a 7 kb Xba I fragment of plasmid pCMB1 deposited at CNCM under accession number I-1317.

5. The nucleotide sequence of claim 1 isolated from *Clostridium bifermantans*.

6. The nucleotide sequence of claim 1 encoding one or more of SEQ ID NO:5, 6, 7, 8, 9, 10, 11, 12 or 13.

7. The nucleotide sequence of claim 1 comprising one or more of SEQ ID NOS:26, 27 or 28.

8. The nucleotide sequence according to claim 1 comprising SEQ ID NO: 29.

9. The nucleotide sequence according to claim 1, wherein said nucleotide fragment encodes a protein P20 having a molecular weight of about 20 kDa, wherein P20 is a precursor of the protein P16, wherein P20 is synthesized during the sporulating phase of bacteria of the species *C. bifermantans*.

10. The nucleotide sequence of claim 1 having the following properties:
said nucleotide sequence comprises an Xba I-Eco RV fragment of the 7 kb Xba I fragment of FIG. 4a and contained in the plasmid pCMB1 deposited at CNCM under accession number I-1317; and
said sequence is about 1.8 kb and encodes a protein having a molecular weight of 66 kDa.

11. The nucleotide sequence of claim 10, wherein said nucleotide sequence encodes a protein P66 wherein said protein has a molecular weight of about 66 kDa, comprises SEQ ID NO:5 at the NH₂ terminal end of said protein and said protein further comprises SEQ ID NO:6.

12. The nucleotide sequence of claim 1 having the following properties:
said nucleotide sequence is present in the 7 kb Xba I fragment of FIG. 4A and contained in plasmid pCMB1 deposited at CNCM under accession number I-1317;
said nucleotide sequence has a size of about 0.5 kb; and
said nucleotide sequence encodes a protein P16, wherein said protein has a molecular weight of about 16 kDa.

13. The nucleotide sequence of claim 12 encoding the protein P16, wherein said protein (1) has a molecular weight of about 16 kDa; (2) comprises SEQ ID NO:12 at the NH₂ terminal end of said protein; and (3) further comprises SEQ ID NO:13.

14. A nucleotide fragment contained in the nucleotide sequence of claim 1 having the following properties:
said nucleotide fragment hybridizes under stringent conditions with the probe 18A;
said nucleotide fragment is present in the 7 kb Xba I fragment represented in FIG. 4A and contained in the plasmid pCMB1 deposited at CNCM under the No. I-1317;
said nucleotide fragment has a size of about 0.55 kb;
said nucleotide fragment encodes a protein P18, wherein said protein has a molecular weight of about 18 kDa.

15. The nucleotide fragment according to claim 14, wherein said nucleotide fragment encodes a protein having a molecular weight of about 18 kDa and said protein comprises SEQ ID NO:7 at the NH₂-terminal end of said protein and said protein further comprises SEQ ID NOS:8–11.

16. A nucleotide probe comprising the nucleotide sequence according to claim 1 or the nucleotide fragment according to claim 14.

17. A recombinant vector comprising the nucleotide sequence of claim 1 at a site which is not essential for replication of said vector.

18. The vector according to claim 17, wherein said vector is the plasmid pCBM1 deposited at CNCM under the number I-1317.

19. The vector according to claim 17, wherein said vector is the plasmid pHT316 further comprising a nucleotide sequence of claim 1.

20. A composition with larvicidal activity comprising, as an active ingredient, recombinant cells comprising the nucleotide sequence of claim 1 or the vector according to claim 17, said cells further comprising a sequence with larvicidal activity of *B. thuringiensis* and/or of *B. sphaericus*.

21. A eukaryotic recombinant cellular host, comprising a nucleotide sequence according to claim 1, or a vector according to claim 17.

22. A prokaryotic recombinant cellular host, comprising a nucleotide sequence according to claim 1, or a vector according to claim 17.

23. The cellular host according to claim 22, wherein said cellular host is a bacterium.

24. The cellular host of claim 23 which is a *C. bifermantans* strain, a *B thuringiensis* strain or a *B sphaericus* strain.

25. The cellular host according to claim 22, wherein said cellular host is a eukaryotic cell.

26. The cellular host according to claim 25, wherein said cellular host is a plant cell.

27. A composition with larvicidal activity comprising, as an active ingredient, recombinant cells according to claim 22.

28. A composition with larvicidal activity according to claim 27, further comprising recombinant cells containing a sequence encoding a polypeptide with larvicidal activity of *B. thuringiensis* and/or of *B. sphaericus*.

29. A polypeptide composition comprising the protein P16 and a protein P18.

30. A polypeptide encoded by the nucleotide sequence of claim 1.

31. A composition comprising the polypeptide of claim 30.

32. A monoclonal antibody directed against a polypeptide according to claim 30.

33. The polypeptide composition according to claim 29 further comprising a protein P66.

34. The polypeptide composition of claim 29, wherein the composition is toxic against mosquitos or simuliids.

35. The polypeptide composition according to claim 29, wherein said composition has the larvicidal activity of a crude extract obtained by:
culturing *Clostridium bifermantans* at 34° C. under anaerobic conditions in TYG medium in a gaseous stream containing 5% $H_2$ 5% $CO_2$ and 90% $N_2$,
recovering the culture at the end of sporulation, after about 16 h,
washing the culture with 1M NaCl,
rinsing twice with a TE buffer, and
recovering the pellet which constitutes the extract.

36. A protein extract having larvicidal activity against the larvae of Diptera, obtained by:
culturing *Clostridium bifermantans* at 34° C. under anaerobic conditions in TYG medium in a gaseous stream containing 5% $H_2$ 5% $CO_2$ and 90% $N_2$,
recovering the culture at the end of sporulation, after about 16 h,
washing the culture with 1M NaCl,
rinsing twice with a TE buffer, and
recovering the pellet which constitutes the extract.

37. A polyclonal antiserum directed against a polypeptide according claim 30 or a composition according to claim 29 or an extract according to claim 36.

38. A polypeptide having larvicidal activity against larvae of Diptera, said polypeptide having the following properties:
said polypeptide is present in an anaerobic bacterium of the species *Clostridium bifermantans*;
said polypeptide does not produce an immunological reaction with sera directed against the crystal proteins of *B. thuringiensis israelensis* or of *B. sphaericus*.

39. The polypeptide of claim 38 having larvicidal activity against mosquitoes or simuliids.

40. The polypeptide according to claim 38, wherein said polypeptide has a molecular weight of about 16 kDa and is the product of expression in a recombinant cell of a nucleotide fragment which hybridizes with the oligonucleotide 16A (SEQ ID NO:1) under stringent conditions, said fragment being contained in the Nsi I-Xba I sequence of the Xba I fragment contained in the plasmid pCMB1 deposited at CNCM under the number I-1317.

41. The polypeptide according to claim 38, wherein said polypeptide has a molecular weight of about 18 kDa and is the product of the expression in a recombinant cell of a nucleotide fragment which hybridizes with the oligonucleotide 18A (SEQ ID NO:2) under stringent conditions, said fragment being contained in the Eco RI-Xba I sequence of the Xba I fragment contained in the plasmid pCMB1 deposited at CNCM under the number I-1317.

42. The polypeptide according to claim 38, wherein said polypeptide has a molecular weight of about 66 kDa and is the product of the expression in a recombinant cell of a nucleotide fragment which hybridizes with the oligonucleotide 66A and/or 66B under stringent conditions, said fragment being contained in the Xba I-Eco RI sequence of the Xba I fragment contained in the plasmid pCMB1 deposited at CNCM under the number I-1317 (SEQ ID NO: 3–4).

43. A polypeptide fragment of a protein according to claim 38, wherein said fragment has larvicidal activity against the larvae of Diptera.

44. The polypeptide fragment of claim 43, wherein the fragment has larvicidal activity against mosquitoes or simuliids.

45. A polypeptide according to claim 38, wherein said polypeptide is recognized by antibodies directed against the protein P16, and/or by antibodies directed against the protein P18, and/or by antibodies directed against the protein P66.

46. The polypeptide according claim 38, wherein said polypeptide comprises an amino acid sequence encoded by at least one of the chains Seq1 (SEQ ID NO:26), Seq2.1 (SEQ ID NO:27), Seq2.2 (SEQ ID NO:28) and is recognized by anti-protein P66 antibodies or encoded by the chain Seq3 (SEQ ID NO:29) and recognized by anti-protein P16 antibodies or, anti-protein P18 antibodies.

47. A composition with larvicidal activity comprising, as an active ingredient, one or more polypeptides according to claim 30.

48. The polypeptide according to claim 38, wherein said polypeptide is modified by addition, deletion, substitution of amino acids provided that it retains toxic activity against the larvae of Diptera.

49. The polypeptide of claim 48 which is toxic against mosquitoes or simuliids.

* * * * *